United States Patent
Ba et al.

(10) Patent No.: US 12,424,323 B2
(45) Date of Patent: Sep. 23, 2025

(54) HYBRID AND ACCELERATED GROUND-TRUTH GENERATION FOR DUPLEX ARRAYS

(71) Applicant: VENTANA MEDICAL SYSTEMS, INC., Tucson, AZ (US)

(72) Inventors: Qinle Ba, San Mateo, CA (US); Jim F. Martin, Mountain View, CA (US); Satarupa Mukherjee, Fremont, CA (US); Yao Nie, Sunnyvale, CA (US); Xiangxue Wang, Cleveland Heights, OH (US); Mohammadhassan Izady Yazdanabadi, Palo Alto, CA (US)

(73) Assignee: Ventana Medical Systems, Inc., Tucson, AZ (US)

( * ) Notice: Subject to any disclaimer, the term of this patent is extended or adjusted under 35 U.S.C. 154(b) by 357 days.

(21) Appl. No.: 18/125,043

(22) Filed: Mar. 22, 2023

(65) Prior Publication Data

US 2023/0307132 A1    Sep. 28, 2023

Related U.S. Application Data

(63) Continuation-in-part of application No. PCT/US2023/015939, filed on Mar. 22, 2023.
(Continued)

(51) Int. Cl.
*G06K 9/00* (2022.01)
*G06V 10/774* (2022.01)
(Continued)

(52) U.S. Cl.
CPC ........... *G16H 50/20* (2018.01); *G06V 10/774* (2022.01); *G06V 10/945* (2022.01);
(Continued)

(58) Field of Classification Search
CPC ...... G16H 50/20; G16H 30/40; G06V 10/774; G06V 10/945; G06V 20/695;
(Continued)

(56) References Cited

U.S. PATENT DOCUMENTS 10,650,520 B1 *  5/2020  Beck ...................... G16H 50/20
2021/0295528 A1 *  9/2021  Fuchs .................. G06V 10/751

FOREIGN PATENT DOCUMENTS

CN    111417958 A  *  7/2020  ........... G06T 7/0012

OTHER PUBLICATIONS

Aresta, G. et al., "iW-Net: an automatic and minimalistic interactive lung nodule segmentation deep network", arXiv:1811.12789v1, Nov. 30, 2018.
(Continued)

*Primary Examiner* — Xin Jia
(74) *Attorney, Agent, or Firm* — MUGHAL GAUDRY & FRANKLIN PC

(57) ABSTRACT

Methods and systems can include: accessing a digital pathology image; generating, using a first machine-learning model, a segmented image that identifies at least: a predicted diseased region and a background region in the digital pathology image; detecting depictions of a set of cells in the digital pathology image; generating, using a second machine-learning model, a cell classification for each cell of the set of cells, wherein the cell classification is selected from a set of potential classifications that indicate which, if any, of a set of biomarkers are expressed in the cell; detecting that a subset of the set of cells are within the background region; and updating the cell classification for each cell of at least some cells in the subset to be a background classification that was not included in the set of potential classifications.

19 Claims, 20 Drawing Sheets

Related U.S. Application Data

(60) Provisional application No. 63/269,833, filed on Mar. 23, 2022.

(51) Int. Cl.
  *G06V 10/94* (2022.01)
  *G06V 20/69* (2022.01)
  *G06V 20/70* (2022.01)
  *G16H 50/20* (2018.01)

(52) U.S. Cl.
  CPC .......... *G06V 20/695* (2022.01); *G06V 20/698* (2022.01); *G06V 20/70* (2022.01); *G06V 2201/03* (2022.01)

(58) Field of Classification Search
  CPC .. G06V 20/698; G06V 20/70; G06V 2201/03; G06T 2207/10056; G06T 2207/20084; G06T 2207/30024; G06T 7/11
  See application file for complete search history.

(56) References Cited

OTHER PUBLICATIONS

Cho S. et al., "DeepScribble: Interactive Pathology Image Segmentation Using Deep Neural Networks with Scribbles", 2021 IEEE 18th International Symposium on Biomedical Imaging (ISBI) Apr. 13-16, 2021, Nice, France.

International Search Report and Written Opinion for PCT Application No. PCT/US2023/015939, dated Jul. 10, 2023.

Sofiiuk, K. et al., "f-BRS: Rethinking Backpropagating Refinement for Interactive Segmentation", 2020 IEEE/CVF Conference on Computer Vision and Pattern Recognition (CVPR).

Wang, G. et al., "Interactive Medical Image Segmentation using Deep Learning with Image-specific Fine-tuning", arXiv: 1710. 0403v1, Oct. 11, 2017.

Weiss, N. et al., "Towards Interactive Breast Tumor Classification Using Transfer Learning", 2015 18th International Conference, Austin, Texas.

"Halo", Image Analysis Platform, Available Online at: https://indicalab.com/halo/, Accessed from Internet on Mar. 24, 2023, 17 pages.

"Pathology Informatics Summit", Digital pathology Place, Mar. 9-12, 2022, pp. 1-5.

Aubreville et al., "Mitosis DOmain Generalization Challenge", 10.5281/zenodo.4573977, 2021.

Ba et al., "Generalizable Deep-Learning-based Interactive Segmentation in Digital-pathology Analysis", PI Summit, 2022, 2 pages.

Boykov et al., "Interactive Graph Cuts for Optimal Boundary & Region Segmentation of Objects in N-D Images", Proceedings of International Conference on Computer Vision, vol. 1, Jul. 2001, pp. 105-112.

Candemir et al., "Lung Segmentation in Chest Radiographs Using Anatomical Atlases With Nonrigid Registration", IEEE Transactions on Medical Imaging, vol. 33, No. 2, Feb. 2014, pp. 577-590.

Carse et al., "Active Learning for Patch-Based Digital Pathology Using Convolutional Neural Networks to Reduce Annotation Costs", European Congress on Digital Pathology, Jul. 2019, 11 pages.

Dasgupta, "Two Faces of Active Learning", Theoretical computer science, vol. 412, No. 9, Apr. 2011, pp. 1767-1781.

Grady, "Random Walks for Image Segmentation", IEEE Transactions on Pattern Analysis and Machine Intelligence, vol. 28, No. 11, Nov. 2006, pp. 1768-1783.

Gulshan et al., "Geodesic Star Convexity for Interactive Image Segmentation", IEEE Computer Society Conference on Computer Vision and Pattern Recognition, Jun. 2010, pp. 3129-3136.

Hariharan et al., "Semantic Contours from Inverse Detectors", Proceedings of the IEEE International Conference on Computer Vision, Nov. 2011, pp. 991-998.

Jaeger et al., "Automatic Tuberculosis Screening Using Chest Radiographs", IEEE Transactions on Medical Imaging, vol. 33, No. 2, Feb. 2014, pp. 233-245.

Li et al., "Interactive Image Segmentation With Latent Diversity", IEEE/CVF Conference on Computer Vision and Pattern Recognition, Jun. 2018, pp. 577-585.

Long et al., "Learning Transferable Features with Deep Adaptation Networks", International Conference on Machine Learning, vol. 37, May 27, 2015, 9 pages.

Mahadevan et al., "Iteratively Trained Interactive Segmentation", British Machine Vision Conference, Sep. 3-6, 2018, pp. 1-12.

Miao et al., "Quick Annotator: An Open-Source Digital Pathology Based Rapid Image Annotation Tool", The Journal of Pathology: Clinical Research, vol. 7, No. 6, Nov. 2021, pp. 1-14.

Moreno-Torres et al., "A Unifying View on Dataset Shift in Classification", Pattern recognition, vol. 45, No. 1, Jan. 2012, pp. 521-530.

Pan et al., "Unsupervised Intra-Domain Adaptation for Semantic Segmentation Through Self-Supervision", In Proceedings of the IEEE/CVF Conference on Computer Vision and Pattern Recognition, Jul. 2020, pp. 3764-3773.

Rother et al., "GrabCut Interactive Foreground Extraction Using Iterated Graph Cuts", ACM Transactions on Graphics, vol. 23, No. 3, Aug. 2004, pp. 309-314.

Ruifrok et al., "Quantification of Histochemical Staining by Color Deconvolution", Analytical and Quantitative Cytology and Histology, vol. 23, No. 4, Aug. 2001, pp. 291-299.

Sener et al., "Active Learning for Convolutional Neural Networks: A Core-Set Approach", In: International Conference on Learning Representations, Jun. 2018, pp. 1-13.

Tzeng et al., "Adversarial Discriminative Domain Adaptation", IEEE Conference on Computer Vision and Pattern Recognition, Jul. 2017, pp. 7167-7176.

Wang et al., "Deep High-Resolution Representation Learning for Visual Recognition", IEEE Transactions on Pattern Analysis and Machine Intelligence, vol. 43, No. 10, Mar. 13, 2020, pp. 1-23.

Wang et al., "Deep High-Resolution Representation Learning for Visual Recognition", IEEE Transactions on Pattern Analysis and Machine Intelligence, vol. 43, No. 10, Apr. 2020, pp. 3349-3364.

Xu et al., "Deep Interactive Object Selection", IEEE Conference on Computer Vision and Pattern Recognition, Mar. 13, 2016, pp. 1-9.

Yosinski et al., "How Transferable Are Features in Deep Neural Networks?", Advances in Neural Information Processing Systems, vol. 27, Nov. 6, 2014, 14 pages.

Yuan et al., "Object-Contextual Representations for Semantic Segmentation", European Conference on Computer Vision, Aug. 2020, pp. 1-18.

Yuan et al., "Segmentation Transformer: Object-Contextual Representations for Semantic Segmentation", European Conference on Computer Vision, Apr. 2021, 21 pages.

Sofiiuk, K., et al., "F-BRS: Rethinking Backpropagating Refinement for Interactive Segmentation," *2020 IEEE/CVF Conference on Computer Vision and Pattern Recognition (CVPR)*, Seattle, WA, USA, 2020, pp. 8623-8632, doi:10.1109/CVPR42600.2020.00865.

Sofiiuk, K., et al., "Reviving Iterative Training with Mask Guidance for Interactive Segmentation." *2022 IEEE International Conference on Image Processing (ICIP)* (2021): 15 pages, doi:10.1109/ICIP46576. 2022.9897365.

Mukherjee, S., et al., "A Deep Learning based Accelerated Method for Generation of Groundtruth Annotations for Chromogenic Duplex Assays," Medical Imaging with Deep Learning (MIDL), 2023, 4 pages.

\* cited by examiner

Tumor : Grey, Stroma : White, Other : Black

HYBRID AND ACCELERATED GROUND-TRUTH GENERATION FOR DUPLEX ARRAYS

CROSS REFERENCE TO RELATED APPLICATIONS

This application claims the benefit of and the priority to International Application Number PCT/US2023/015939, filed on Mar. 22, 2023, which claims the priority to U.S. Provisional Application No. 63/269,833, filed on Mar. 23, 2022. Each of these applications is hereby incorporated by reference in its entirety for all purposes.

FIELD

The present disclosure relates to digital pathology. Exemplary embodiments relate to generating ground-truth data for multiplex assays.

BACKGROUND

Digital pathology involves scanning of the slides (e.g., histopathology or cytopathology glass slides) to produce digital images. The slides can include biosamples (e.g., tissue slides or bioliquids) that have been stained using one or more stains (i.e., dyes) that selectively bind to particular cellular components or tissue types. The digital images may be subsequently processed by using a digital-pathology image-processing technique and/or by being interpreted by a pathologist. This subsequent processing may be used for a variety of reasons, such as predicting or facilitating a diagnosis of a disease, estimating a degree to which a given therapy has been effective for a given subject, predicting a degree to which a given therapy will be effective for a given subject, and/or facilitating the development of a new treatment (e.g., new active agent, dosage, composition, treatment schedule, etc.

A traditional approach for analyzing digital pathology images is for a trained human pathologist to examine highly magnified portions (i.e., "fields of view") of a slide and to manually segment the image to identify one or more portions of interest (e.g., so as to exclude background, artifacts, macrophages, etc.) and to then detect and classify signals within the remaining portion(s) of the image. The segmentation and classification are typically performed at a magnification of 40×-400×. Therefore, when the standard approach is used, generating digital pathology results is a very labor-intensive, time-intensive, and financially expensive effort.

An alternative approach is to use a machine learning model to process digital pathology images. However, this typically involves training the model using a training data set that includes a large number of manually labeled images that are then defined as a ground truth (for the model to use to learn parameter values).

As explained above, producing these labeled images is tedious and time-consuming to collect. Furthermore, obtaining training images may be difficult due to privacy concerns. Currently, to collect images to use as ground truth to train a model, the samples to be labeled may be randomly selected from the pool of data (e.g., available images). However, randomly picking the samples or the number of samples to be labeled is not an efficient approach. Randomly selected samples may not be the most informative ones in training a machine learning model. Therefore, labeling them is often a waste of resources (e.g., pathologist time), without adding any significant value to the training process.

The size of a training set required to train a machine learning model typically scales with the complexity of the model. Meanwhile, the more complex models often produce results with higher accuracy and precision. For example, deep-learning (DL) models are becoming increasingly used in the medical field. However, there is no single DL model that can be applied for all use cases, or even for all medical use cases. For example, natural-scene images have very different characteristics that medical images (e.g., digital pathology images). Further, different types of medical images may have different characteristics. For example, the characteristics of digital pathology (DP) images, Immunohistochemistry (IHC) images, Hematoxylin and eosin (H&E) images, IHC images targeting different proteins (e.g., Ki67 vs. CK7), are very different.

For example, processing lab results, MM scans, digital-pathology scans (or even scans that use different stains), and patient medical records are all very different types of processing that likely require different pre-processing, loss functions, model architectures, etc. Beyond that, the implementations of DL in the medical field remain incredibly limited relative to the implementation of DL for processing natural-scenes data, which may be due to the availability of the latter and the increased privacy restrictions pertaining to the former.

Thus, despite the power of deep-learning systems, developing such systems and promoting their broad applications in the clinical field is challenging. Deep-learning models often are configured to learn values for thousands of parameters. The quantity of training images in a training data set used to train a model is typically one or more orders or magnitude higher than the number of parameters.

Digital pathology is a particularly challenging context for training any model, much less DL models. In digital pathology, the stains that are used are highly variable. Further, multiple biomarker dyes are frequently used, meaning that there are even fewer images available (particularly when considering privacy constraints) that depict samples stained with a particular combination of dyes. It is often the case that a DL model built for a specific dataset (i.e., a specific image domain) fails to perform well even on a similar or related dataset (another different image domain). In DP, a model designed for a specific diagnostic assay is not readily reused for another assay due to performance issues. This is also the case when applying a model to the images from the same slides but scanned from a different scanner. Thus, a model that can be easily generalized to multiple assays or across different image domains is desirable.

Therefore, it is particularly challenging to process digital pathology images to segment regions of interest. Further, even if a model is configured to perform this type of segmentation, existing systems are not configured to receive responsive user input that does not lead to overfitting or to generating a model's utility to be diminished.

Additionally, while the analysis of heterogeneous tumor microenvironment promises significant benefit to clinical practice, such analysis is very complex. Recent years have seen an increasing need to leverage new multiplexing immunohistochemistry (mIHC) assays to guide patient stratification in immunotherapy, because mIHC enables the accurate characterization of the interactions between cancer-related proteins expressed in different types of cells in the tumor microenvironment.

Cytokeratin (CK7) and Programmed death-ligand (PDL1) are individually important biomarkers for the clinical diagnosis of lung cancer as they guide the characterization of how subjects respond to immunotherapies. The expression of CK7 is cytoplasmic and membranous, whereas that of PDL1 is membranous. The antibody clone used in this study for PDL1 is SP263. Duplex immunohistochemistry staining (duplex) of tissue sections allows simultaneous detection of two biomarkers and their co-expression at single-cell level. Duplexes are often difficult or impossible for a human to reliably score, and therefore, an automated technique for assisting the scoring of each assay is necessary.

In order to analyze the images from each mHIC assay, three major technology elements need to be developed—(i) Groundtruth Creation (GT) (ii) Phenotype Detection (iii) Measurement of Expression Levels. For example, a machine learning model that accurately detects signals in duplex images would be highly valuable. However, training such a model likely requires a tremendous amount of training data that includes—for each of many duplex images—accurate labels that identify the signals of each biomarker. Detecting such accurate labels in a duplex image may be difficult or impossible for a human, due to potential co-expression of biomarkers. Thus, it may be difficult or impossible to collect any accurate data, much less a large quantity of accurate training data.

SUMMARY

In some instances, a computer-implemented method is provided that included: accessing a digital pathology image that depicts a tissue slice stained with multiple stains, each of the multiple stains staining for a corresponding biomarker of a set of biomarkers, wherein the multiple stains include at least three stains; generating, using a first machine-learning model, a segmented image that identifies at least: a predicted diseased region in the digital pathology image; and a background region in the digital pathology image, wherein the background region indicates that signals that are present within the background region are not to be assessed when analyzing signals of the set of biomarkers; detecting depictions of a set of cells in the digital pathology image; generating, using a second machine-learning model, a cell classification for each cell of the set of cells, wherein the cell classification is selected from a set of potential classifications that indicate which, if any, of the set of biomarkers are expressed in the cell; detecting that a subset of the set of cells in the digital pathology image are within the background region; and in response to detecting that the subset of the set of cells in the digital pathology image are within the background region, updating the cell classification for each cell of at least some cells in the subset to be a background classification that was not included in the set of potential classifications.

In some instances, the second machine-learning model (or another machine-learning model) may further perform a detection of each cell of the set of cells. In some instances, the second machine learning may perform and the updating may update a cell segmentation and/or cell instance segmentation in addition to or instead of a cell classification.

The method may include: generating a training data set that includes the digital pathology and that includes an updated set of cell classifications that includes the updated cell classification for each cell in the subset; and training a third machine-learning model using the training data set.

The method may include: detecting that each cell in another subset of cells in the digital pathology image has a cell classification that is inconsistent with a region in which the cell is depicted as being located; and setting a confidence metric for the cell classification of each cell in the other subset to be lower than a confidence level associated with different cell classifications that were not detected as being inconsistent with the region in which the cell is depicted as being located; wherein the third machine-learning model is trained using the confidence metrics.

The method may include: generating a new set of cell classifications by processing a different digital-pathology image using the third machine-learning model, wherein a new subset of the new set of cell classifications correspond to the background classification; generating one or more metrics corresponding to a predicted diagnosis, prognosis or treatment response using the new set of cell classifications; and outputting the one or more metrics.

The third machine-learning model may include a U-Net architecture.

Updating the cell classification for each cell of the at least some cells in the subset to the background classification may include automatically update the cell classification for each cell of all cells in the subset to the background classification.

The method may include configuring a graphical user interface (GUI) to present an interactive screen that: displays at least part of the segmented image; displays, for each of at least some of the set of cells, a representation of the cell that indicates both the cell classification and a location of the depiction of the cell in the digital pathology image; and provides a tool configured to receive input from a user that indicates an instruction to change one or more of the cell classifications of the at least some of the set of cells; detecting an interaction with the tool that represents an instruction to change the cell classification of a particular cell of the at least some of the set of cells; and updating, in response to the detected interaction, the changed cell classification for the particular cell, wherein the updated set of cell classifications includes the changed cell classification for the particular cell.

The method may include detecting that each cell in another subset of cells in the digital pathology image has a cell classification that is inconsistent with a region in which the cell is depicted as being located; and automatically changing the cell classification of each cell in the other subset.

The method may include: generating one or more metrics corresponding to a predicted diagnosis, prognosis or treatment response using the set of cell classifications; and outputting the one or more metrics.

The GUI may be configured such that a region in the segmented image is depicted using a color that is representative of the type of region.

For each stain of the set of stains, a target of the stain may be a nuclear target.

For each stain of the set of stains, a target of the stain may be a cell-membrane target.

In some embodiments, a system is provided that includes one or more data processors and a non-transitory computer readable storage medium containing instructions which, when executed on the one or more data processors, cause the one or more data processors to perform part or all of one or more methods disclosed herein.

In some embodiments, a computer-program product is provided that is tangibly embodied in a non-transitory machine-readable storage medium and that includes instructions configured to cause one or more data processors to perform part or all of one or more methods disclosed herein.

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification and variation of the concepts herein disclosed may be resorted to by those skilled in the art, and that such modifications and variations are considered to be within the scope of this invention as defined by the appended claims.

BRIEF DESCRIPTIONS OF THE DRAWINGS

Aspects and features of the various embodiments will be more apparent by describing examples with reference to the accompanying drawings, in which.

Figure 13:
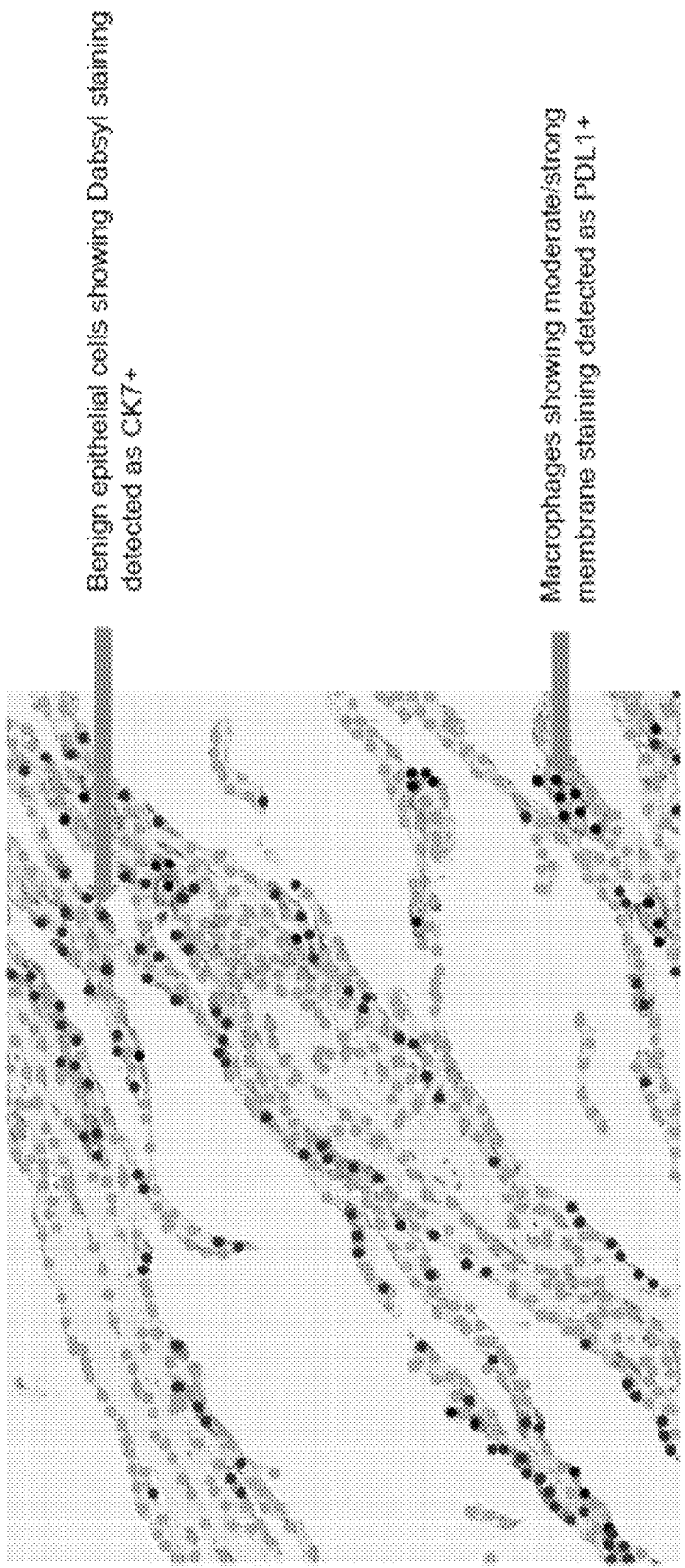

FIG. 13 overlays representations of exemplary HALO cell classifications with an exemplary corresponding digital pathology slide.

Figure 14:
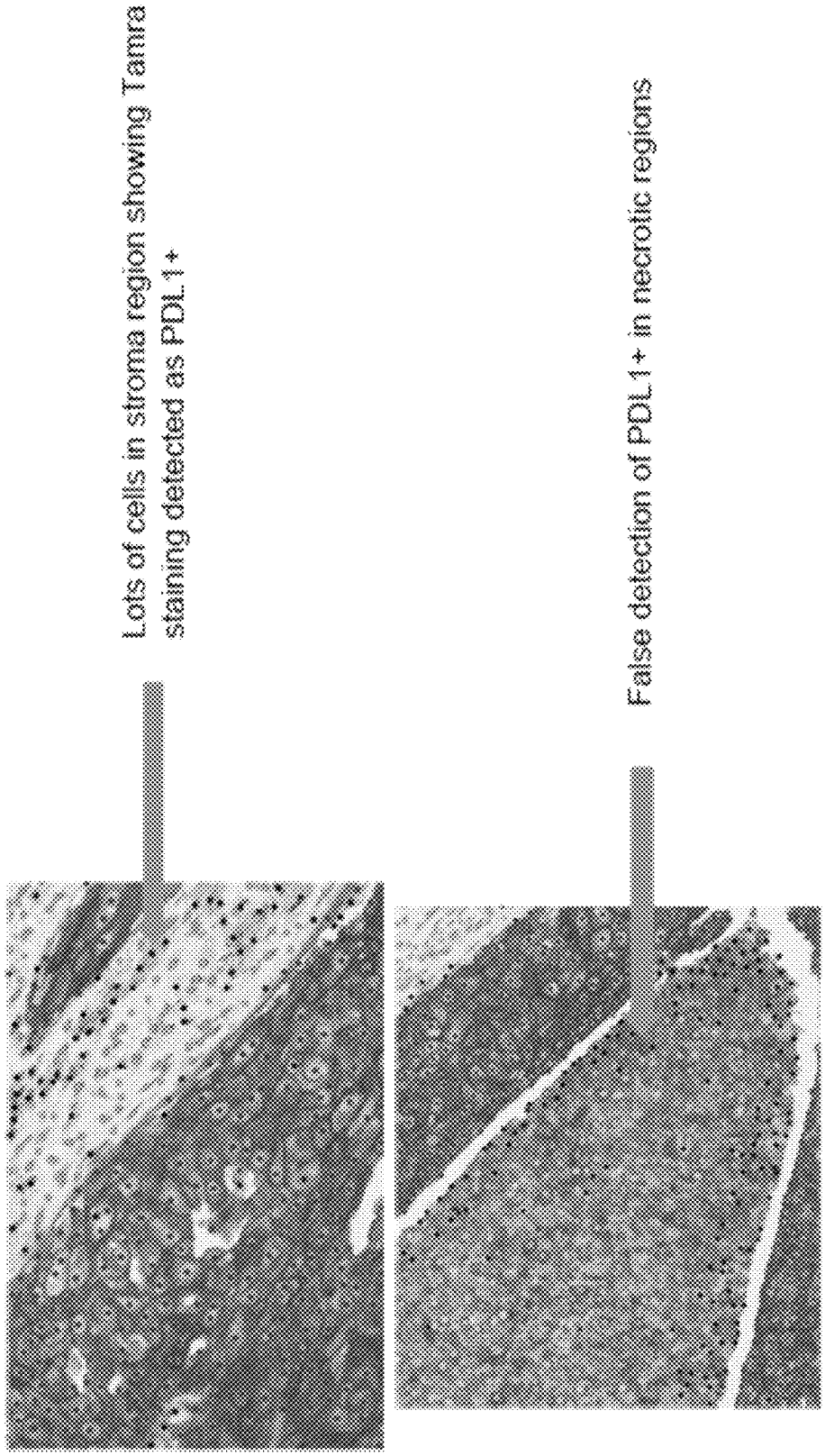

FIG. 14 illustrates exemplary inconsistencies of the HALO outputs.

Figure 15:
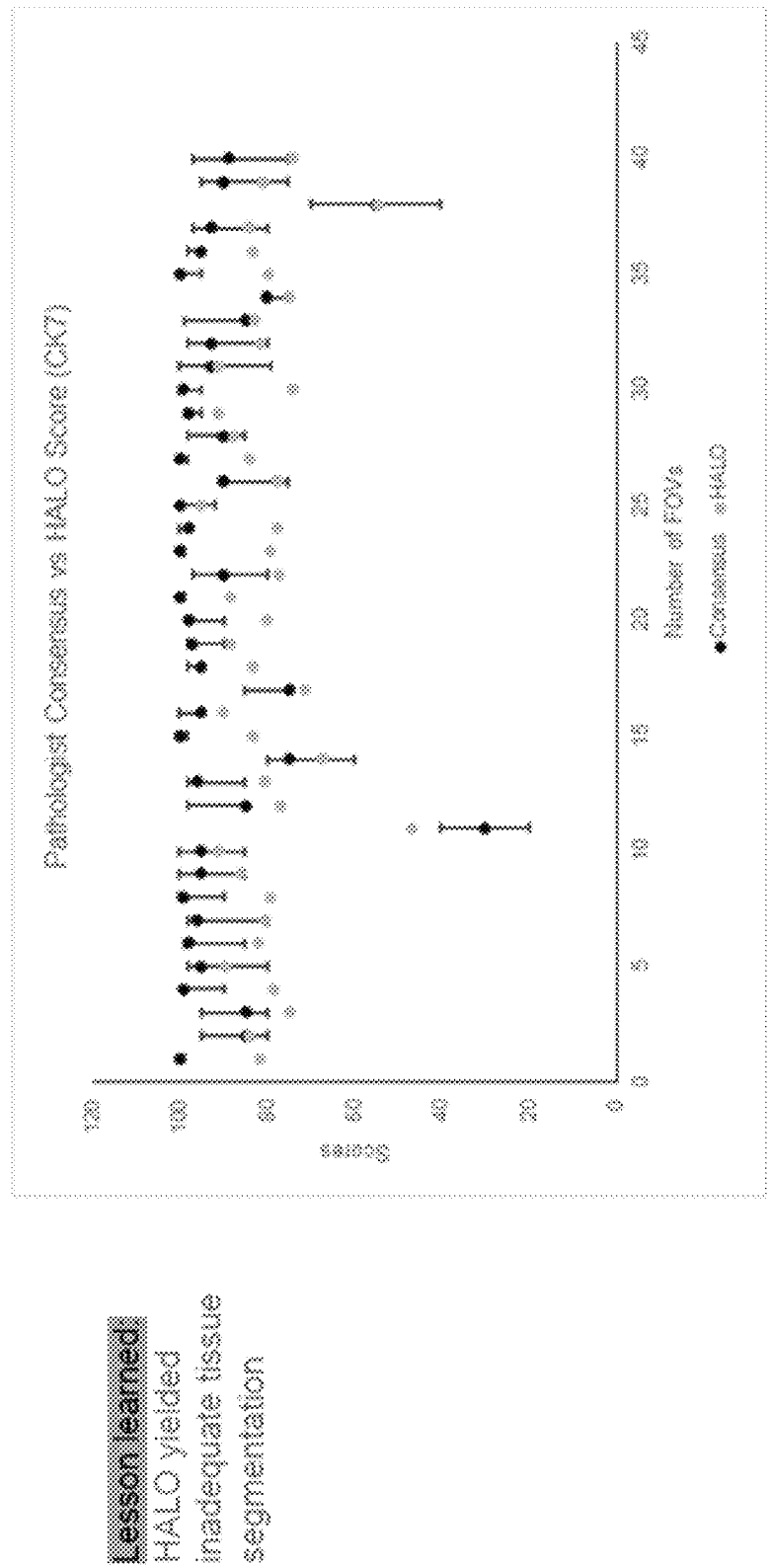
Figure 16:
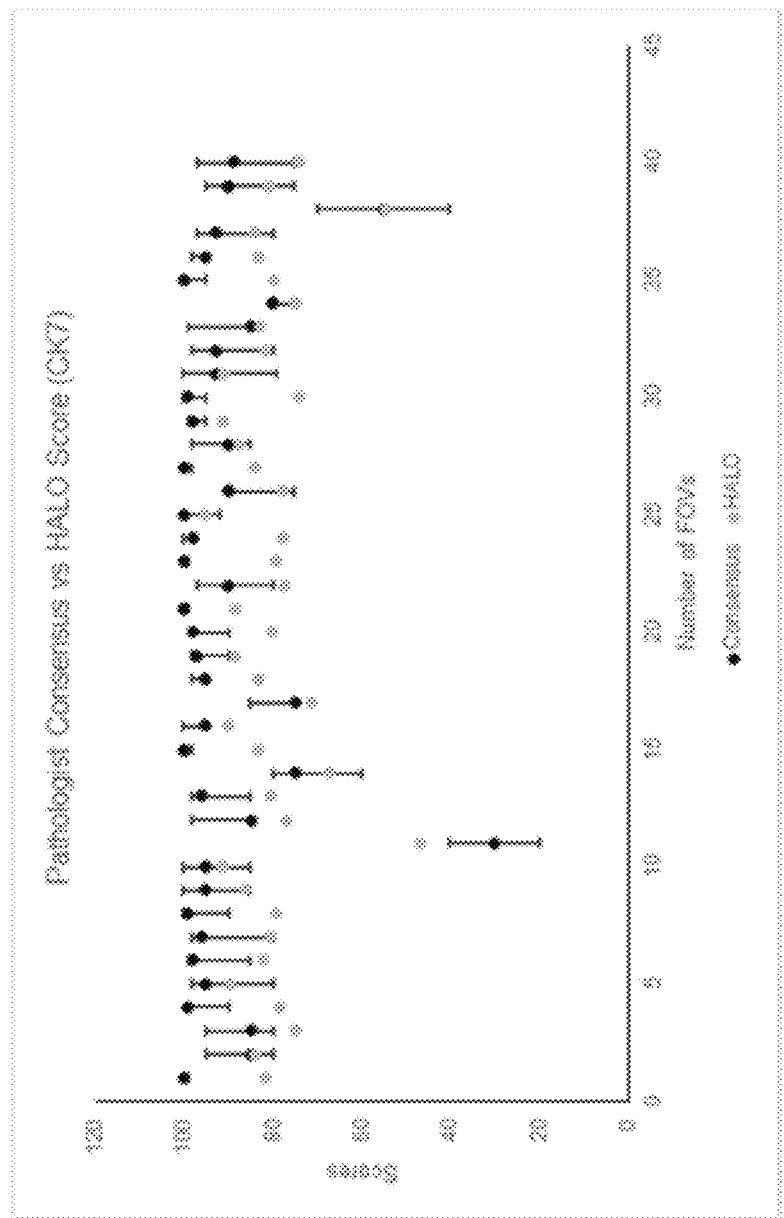

FIGS. 15 and 16 illustrates how exemplary scores representing relative quantities of PDL1-positive and CK7-positive cells (respectively) were determined based on the HALO results compared to the relative quantities based on assessments from the consensus scores based on reviews from three pathologists.

Figure 17:
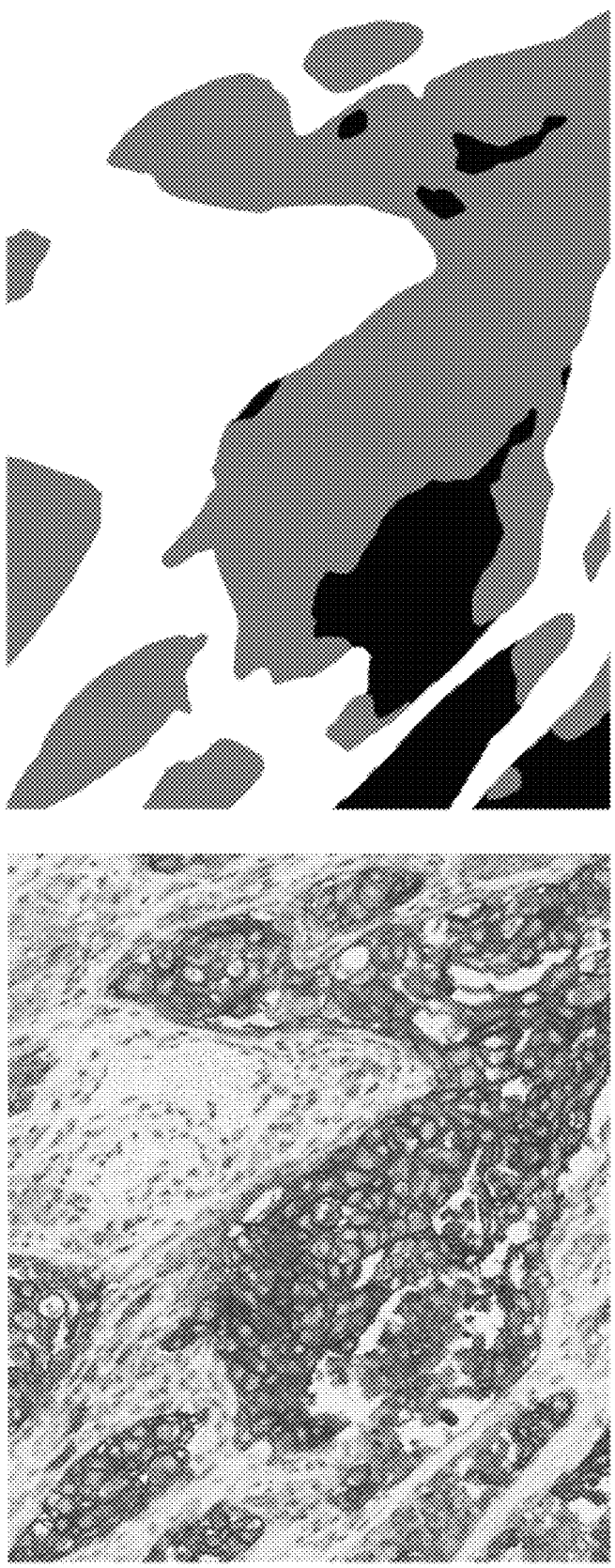

FIG. 17 illustrates tissue segmentation performance using the deep-learning model trained with multi-class data relative to the HALO segmentation.

Figure 18:
Figure 18:

FIG. 18 illustrates classification results.

Figure 19:
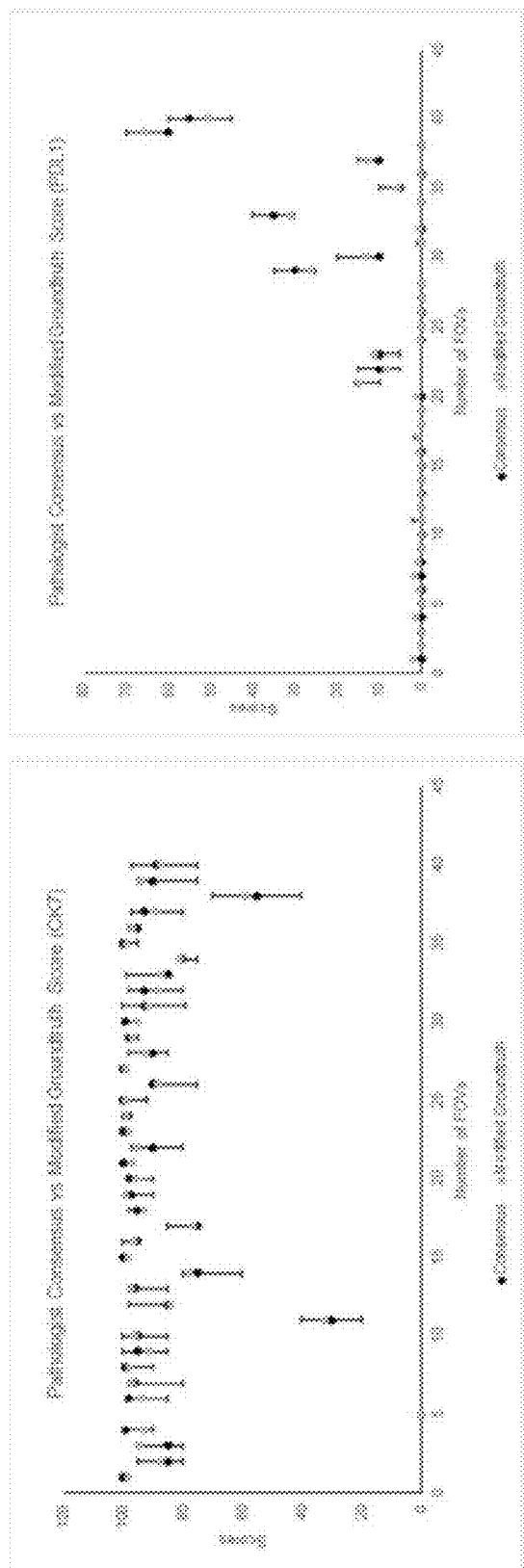

FIG. 19 show exemplary scores representing a relative quantities of PDL1-positive and CK7-positive cells (respectively).

Figure 20:
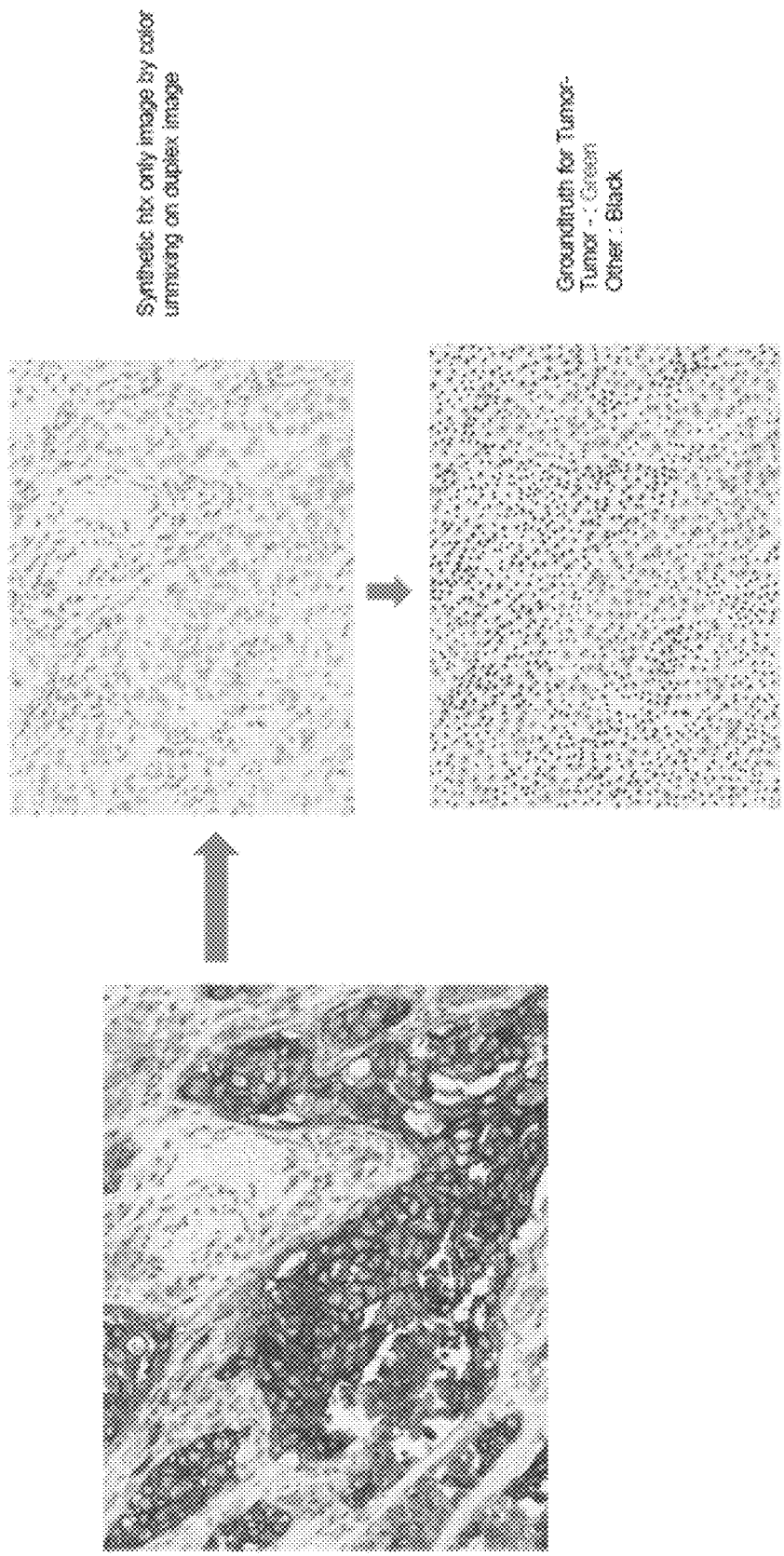

FIG. 20 provides a further example how processing of a digital pathology image (left image) differs depending on whether a traditional color unmixing technique is performed to attempt to isolate tumor signals (top right) or whether the above-identified approach (of modifying HALO cell classifications based on regions identified using a deep-learning model, bottom right).

In the appended figures, similar components and/or features can have the same reference label. Further, various components of the same type can be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

While certain embodiments are described, these embodiments are presented by way of example only, and are not intended to limit the scope of protection. The apparatuses, methods, and systems described herein may be embodied in a variety of other forms. Furthermore, various omissions, substitutions, and changes in the form of the example methods and systems described herein may be made without departing from the scope of protection.

Overview

Various embodiments of the invention relate to training and/or using a deep learning model for interactive segmentation digital pathology images to identify different regions within the image. Further, a graphical user interface (GUI) can be availed, which can allow a user to provide an image, provide interactions to facilitate the segmentation, and/or provide (subsequent to the segmentation) region-label updates. Thus, the deep learning model provides nearly real-time segmentation results, and the GUI is efficiently configured to allow a human reviewer to very efficiently and quickly identify region labels.

Various embodiments relate to using the region labels to update initial cell classifications generated by a cell classification model. The initial cell classifications may indicate—for each cell and for each of multiple biomarkers—whether the cell absorbed a stain that stains for the biomarker. Specifically, the region labels may include one or more labels that convey a biological meaning (e.g., a tumor region or a stromal region), and the region labels may also include a background label that indicates that the corresponding regions are predicted not to include cells pertinent to an analysis of interest. For example, a region labeled "background" may depict a tissue fold, background, an artifact, a macrophage, etc. A given region label may be inconsistent with a classification of a cell that is within the region. For example, it may be inconsistent to have a classification that indicates that a cell does or does not include a biomarker when a depiction of the cell is within a background region. This inconsistency may indicate that (for example) the background region label indicates that no cells are depicted, that any depicted cells do not pertain to the analysis of interest, and/or that an artifact or image defect sufficiently obstructs visualization of signals such that exclusion of corresponding data is preferred.

Thus, an inconsistency between a given region being assigned the background region label and cells being assigned a label that indicates whether the cell absorbed one or more stains may trigger further processing. In some instances, the label for all cells assigned to the region assigned the background region label may be changed to a "background" cell-classification label (e.g., such that the number of potential labels. In some instances, an alert or indicator can be availed to a user to identify the inconsistency. Such an alert or indicator may be provided within an interface or may identify an interface that may include a tool that is configured to receive input to change (or confirm) a classification of a cell and/or to change (or confirm) a region label. The interface may, but need not, be the same interface as one that was configured to receive input identifying labels for the segmented regions.

The interface may show part or all of the digital pathology image (so as to depict the cell) and may further indicate region labels (e.g., by a color or shading). If a user indicates that a cell classification is to be changed, the cell classification data may be updated to include any changed classification. The updated cell classifications may be included in training data that is used to (for example) train another machine-learning model (e.g., that corresponds to a same set of stains associated with the training data) or to generate one or more metrics that may be used to predict or determine (for example) a diagnosis, prognosis, disease progression, response to a given treatment, etc.

Training Images and Click Annotations

The deep learning model can be trained using a multi-class training data set that has images and corresponding annotations from one or more domains. The annotations may include segmentation annotations, that identify borders of or areas of depictions of different things. The annotations may (but need not) include—for each indicated segment—a class (or label, used interchangeably herein) for the segment. The annotations may include, or may be based on, click annotations. For example, for a given image, each of multiple points can be identified, where each point is within a segment that depicts a particular type of object, person, or being. For each point, the annotation may indicate to which of multiple classes the corresponding segment is assigned.

The multi-class training data set identifies segmentations for multiple types of depictions. For example, for a digital pathology image, the classes may include a stroma region, a tumor region, and a background region. As another example, for a natural scene image, the classes may include each vehicle, each stoplight, and the background (all other portions of the image). A background class can be defined to include depictions of (a) other objects that are not selected from the original mask, as well as (b) pure background, where no objects are annotated in the original mask.

That said, the multiple classes need not have semantic meaning. For example, in a three-class instance, the classes may correspond to: a first type of region; a second type of region; and a background region (which may, but need not, include one or more other types of regions). What constitutes the first and second types of regions may be arbitrary. To illustrate, for an image of vehicles at a traffic light, the first type of region may be vehicle, stoplight, person, crosswalk, etc. In a case where an image depicts multiple objects of a given selected type (e.g., multiple vehicles, multiple people, etc.), all such depictions may be considered as being of the same selected type of region.

The number of click annotations that are identified for a given training image may, but need not, be predefined. For example, an implementation may be configured such that each training image is associated with one click annotation per class, three click annotations per class, six click annotations total, ten click annotations total, etc.

In some instances, click annotations are automatically identified for training images. For example, some training images may be associated with a ground-truth mask that indicates (or that can be used to determine) to which label each pixel is to be assigned. Such ground-truth masks may change with different click annotation targets. For example, two out of multiple image regions in an input image can be used as an segmentation target and the corresponding ground-truth mask can be generated to indicate the target image regions and ignore rest of the image regions. The same image can also be paired with click annotations targeting another set of image regions and corresponding ground-truth masks for these specific image regions. For each ground-truth masks specific to a set of click annotations, the image regions can belong to one class or two classes. The number of unique labels in a ground-truth mask may be different from a number of classes for which the deep-learning model is to be trained. When there are more unique labels than classes, a subset of the labels can be selected, where the number of labels in the subset is equal to the number of classes minus one (given that a background class can be used). The selection can be (for example) a random selection, arbitrary selection, or biased towards labels associated with the most pixel assignments. When there are fewer unique labels than classes, the corresponding image can be discarded from the training data set.

Using the click annotations, a ground-truth mask can be generated for each image, which can be used to train the deep-learning model. Using the click annotations, additional input maps can be generated for each image, which can be used to train the deep-learning model. The input map (which may be the same size as the input image) may be generated by encoding the click annotations using a map, such as a disk map or Euclidean distance map. Disk maps, for example, can be generated by starting with an image of value zeros, changing pixel values to 1 (or another positive value) in the clicked pixels and then changing the values of pixels surrounding these clicked ones to 1 to expand the click neighborhood into disk-shaped image regions of value 1. Click maps can be generated by setting values of the clicked pixels (and only the clicked pixels) to be different than the rest of the pixels. Square maps can be generated to include square-shaped regions surrounding clicked pixel locations. In some instances, a single map indicates positions of clicks of multiple classes. In some instances, a separate map is generated for each class.

The masks can be used together with the input image as model training and/or inference input to inform the model where the user input are, so that the model can generate segmentation masks according to where the users click. In training, the model can be trained how to respond to any objects in an image that users would like to target and provide click input for. In inference, the model can predict a target image region/object according to where the user clicks (there can be many objects in an image and the model can use the click locations to predict which object/image region the user intends to segment).

These encodings are further detailed in K. Sofiiuk, I. Petrov, O. Barinova, A. Konushin, F-BRS: Rethinking backpropagating refinement for interactive segmentation, in: 2020 IEEE/CVF Conference on Computer Vision and Pattern Recognition (CVPR), IEEE, 2020, pp. 8623-8632. doi:10.1109/cvpr42600.2020. 00865 and in Sofiiuk, Konstantin, Ilia A. Petrov, and Anton Konushin. "Reviving Iterative Training with Mask Guidance for Interactive Segmentation." arXiv preprint arXiv:2102.06583 (2021), each of which is hereby incorporated by reference in its entirety for all purposes.

Because the classes in the training data need not have semantic meaning, the deep learning model trained on the training data can be configured to provide segmentation in a manner separate from region labeling. Thus, the deep learning model may be configured to predict which portions of an image correspond to different things without predicting what type of thing is depicted in a given portion and/or without predicting whether multiple portions depict the same type of thing. Because of this, a multi-class training data set may be used that includes images and annotations from multiple domains.

Domains may include, for example, digital pathology datasets, natural-scene image datasets, immunohistochemistry datasets, H&E datasets, or any other appropriate image-annotation pair dataset as would be understood by one skilled in the art. Using training data from one or more domains other than digital pathology (e.g., potentially in addition to training data from the digital-pathology domain), a larger training set can be collected. However, by continuing to include digital pathology images in the multi-class training data set, the deep learning model may be readily applied to process multiple types of digital pathology images without substantial additional model development. In some instances, however, the training data set does not even include training data from a domain in which the trained deep learning model is later used for image annotation.

Deep-Learning Model and Training

The deep learning model can include a neural network with more than three, more than four, or more than five layers (including the input and output layers). The deep learning model can include a convolutional neural network.

The deep learning model can be trained using the training data described here (e.g., that includes multi-class images and that may include ground-truth masks and/or click annotations), such that it learns how to segment a particular number of classes (e.g., two target classes and one background class). The training data enforce network learning of effective representations to match the segmentation prediction that correspond to specific pixels indicated via click annotations (or to specific regions within a ground-truth mask). For example, such a model learns to segment any targeting regions pointed to by these pixel locations. It is thus trained to group together the image pixels of unified labels (i.e., similar/identical network representations) as the "annotated" image pixels, no matter what exact underlying semantic meaning they have. In other words, this model need not learn to differentiate the specific semantic classes in an image, but rather can learn to identify semantically similar image regions with the "annotated" pixels and only group these pixels together to generate a segmented target region. Due to such a design, the interactive deep-learning model is capable of identifying any target object or region a user provides click annotations for and does not require domain-specific training to identify the exact classes of regions. Therefore, such embodiments provided herein pose little restrictions on whether test image and training image come from the same domain. This feature is the key to the powerful capability to generalize across image domains.

Accordingly, the trained deep learning model can be used to process other images to generate predicted segmentation annotations.

In some instances, a user may provide click annotations with an input image. For example, the user may select or upload an image using a GUI. The GUI may then present the image and avail tools to add click annotations. The click annotations may identify—for each of a set of classes—one or more pixels in the image that do, or that do not, correspond to the class. The deep-learning model may use the click annotations and the learned model parameters to predict which portions of the images correspond to each of the set of classes.

In some instances, a user provides an input image but no click annotations. The deep-learning model may then use the learned model parameters to identify a set of segments. The model may attempt to assign labels based on similarities across various regions or may provide merely the segmentation data (e.g., identifying pixels on boundaries of various segmentation regions).

In some instances, an output of a trained deep learning model may include one or more values for each pixel. The value(s) may include a class assignment (e.g., Class 1, 2, or 3). In some instances, a value may include an error indicating that a class was not assigned. The output may include a set of masks—each of which correspond to a given predefined class. Each mask may include a value for each pixel, where a particular value (e.g., 1) indicates that it is predicted that the pixel is part of a region (or a perimeter of the region) of the class and another particular value (e.g., 0) indicates that it is predicted that the pixel is not part of a region (or a perimeter of the region) of the class. Alternatively, a value for each pixel may represent a predicted likelihood or confidence that the pixel is part of a region of the class.

Interactive GUI for Efficient Label Identification

After the deep learning model processes an input image, a GUI can be generated or a GUI (e.g., the same GUI as used to provide click annotations) can be updated to represent segmentations generated via the processing.

Specifically, the GUI can be configured to receive corrections for any labels and/or to identify—for each of one or more regions—a region label that is to be assigned to the region. For example, input-translation definitions may be created that indicate—for each of multiple particular types of mouse clicks—what the updated region label is to be. To illustrate, a single left click may correspond to a tumor region; a single right click may correspond to a stroma region; and a double left click may correspond to a background region. If a user then performs any of these types of clicks within a depiction of a given segmented region, the region label of the region may be updated or defined accordingly.

As another example, the GUI may be configured such that a pull-down menu (identifying different potential region labels) appears after a user clicks within a given region. The pull-down menu may identify the potential region labels, and the user may select which region label is to be assigned to the region.

In this manner, regions can be quickly identified and classified very quickly in a manner that requires little time investment by the user (e.g., as compared to traditional manual segmenting and manually identifying a region label for each region). For example, an image tile of 600×600 pixels in size can be segmented in less than a minute, and the GUI can facilitate rapid identification of region labels, which can result in real-time updates to region labels and updates to the GUI that are intuitive to users and facilitate further region-label identifications.

The label identifications may quickly or immediately trigger an update of the labels.

Cell Classification

A cell-classification machine-learning model may separately process the digital-pathology image to classify each cell detected in the model. The cell detection and the cell classification may be performed by the same cell-classification machine-learning model or by another machine-learning model. The cell-classification model may include all or part of the HALO AI model. In some instances, the cell-classification machine-learning model is configured to predict the cell classifications based, at least in part, on regions and/or region labels that are different from those as identified via techniques disclosed herein (e.g., using a model trained using multi-class data and/or using an interactive GUI).

The classification may correspond to a cell-classification label that represents a prediction as to whether—with respect to each of multiple biomarkers—the depicted cell is positive or negative for the biomarker. In some instances, a first stain (e.g., and H&E stain) is used to detect cells within the digital-pathology image and a cell-classification label is determined based on signals from the other stain(s).

Cell Classification Updates

One or more rules may be defined that relate to a consistency of the classification of a cell and the classification of a corresponding region. For example, if a region has been identified as a background region, it may be inconsistent with a cell depicted within the region having a label that may be subsequently used to generate an output metric. Thus, one or more rules may be defined to facilitate reducing such inconsistencies.

The platform may be configured to allow a given cell to be assigned to a background cell classification, even if a similar classification was not present or available when using the cell-classification model. For example, the cell-classification model may produce labels that include combinations of being positive or negative for each of multiple biomarkers but not having a label option that indicates that a cell is to be not considered for biomarker analyses. Meanwhile, the classification update may avail such a label.

One exemplary rule is configured such that any non-background cell-classification is to be changed to be a background cell-classification if its depiction is located within a depiction of background region. One exemplary rule is configured such that a discrepancy between one or more cell classifications and a corresponding region label triggers a relabeling or reshaping of the region. For example, a rule may be configured such that if classifications of at least a threshold percentage of cells within a specified area (e.g., generally or an area with an edge on a border of the region) are indicative of the cells being tumor cells and if the tumor is designated as a stroma region, the region either be reclassified as a tumor region or shrunk to not include at least part of the specified area.

One exemplary rule is configured such that an alert is to be sent or presented to a user under any of one or more condition satisfaction. An illustrative condition satisfaction is when a cell has been assigned a classification other than a background cell classification despite the cell being depicted as being within a region that has been labeled as a background region. Another illustrative condition satisfaction is when a cell has been assigned a classification that is indicative of or consistent with the cell being a tumor or cancer cell despite a depiction of the cell being within a region assigned to a non-cancer region label (e.g., a stromal label).

An interface may then be updated or generated in real-time or with delay to convey the location of the cell, the current classification of the cell, and at least part of the region. The interface may include at least a portion of the digital pathology image that includes a high-resolution image of the cell, a depiction of the intensity of one or more stains (e.g., across the cell), and/or a depiction of the boundaries of and/or a label for the corresponding segmented region.

An interface availed to the user via the alert may be configured to receive input that indicates that a classification of one or more cells is to be changed (or confirmed), that a classification of a segmented region is to be changed, and/or that an area of a segmented region is to be changed. For example, the interface may include a tool that allows a user to select an alternative classification for a cell or an alternative label for a region (or to confirm a cell classification and/or region label). As an alternative or additional example, the interface may include a tool that allows a user to indicate a changed area for a segment region (e.g., by drawing a new perimeter of the region, moving dot markers that indicate the perimeter, or de-selecting cells to be included in the region).

Exemplary Practical Applications

The cell classifications and/or the region labels may be used to generate or as part of ground-truth data to train a machine-learning model (e.g., that includes a U-Net architecture) to process digital pathology data. The machine-learning model that is trained using the ground-truth data may be different from any model used to generate segmented regions, to detect individual cells, and/or to generate initial cell classifications.

The cell classifications and/or the region labels may be used, alternatively or additionally, to generate one or more metrics or recommendations to support a care provider determining a diagnosis, prognosis or treatment recommendation for a subject. For example, an exemplary metric may include a count of a number of cells assigned a given classification, which may be normalized based on (for example) a number of total cells detected, a number of cells detected that were not assigned to the background classification, and/or a number of cells detected that were assigned to another classification. An exemplary metric may include an absolute cumulative area of each of one or more types of regions (e.g., tumor regions and/or stroma regions) in one or more digital pathology images and/or a relative cumulative area of tumor regions in one or more digital pathology images (e.g., relative to a sum of the areas of the tumor and stroma regions). In some instances, a change metric is generated that indicates an extent to which a cumulative absolute or cumulative relative area has changed relative to a comparable metric generated by processing digital pathology images corresponding to a same subject but a prior time point. The change metric may identify a difference or a percentage change or be based on a loss function of the typical kind used in optimization and artificial neural networks.

The region labels may further or alternatively be used (for example) to facilitate performing digital pathology analyses that include characterizing cells depicted in the images. For example, background colors representing the region labels may be provided in a digital-pathology interface presented to facilitate segmenting and/or labeling individual cells. As another example, the region labels may be used to assess one or more rules that determine whether there is a potential inconsistency (or an actual inconsistency) with a cell label and a region label. If so, an alert may be presented or sent to request review of the inconsistency.

Exemplary Advantages

Some embodiments disclosed herein relate to techniques that facilitate improving the accuracy of cell classifications by analyzing data generated by two separate machine-learning models (e.g., where one model predicts segmented-region labels and another model predicts classifications of cells). The improvement may include automated updates of select cell classifications and/or region labels and/or facilitating (e.g., via communications and/or an interface) conveying a potential inaccuracy (e.g., corresponding to a label inconsistency) to a user and supporting an update for a cell classification or region label to address the issue. A GUI may be configured to represent the potential inaccuracy and to provide one or more tools to allow a user to change one or more cell classifications and/or one or more region labels.

Some embodiments disclosed herein provide a platform that supports simultaneous segmentation of more than two types of regions and that shows success in DL-based inter-action segmentation being applied across distinct imaging modalities. Techniques disclosed herein have distinct performance advantages over alternative approaches. Advantages include being capable accurately and reliably performing binary or three-class segmentation (e.g., in a manner that supports accurate and reliable metric generation); providing interactive user-guided segmentation to efficiently integrate user know-how and to increase interpretability of results; and being able to generalize across image modalities, tissue types and staining patterns. Further examples of advantages of embodiments of the invention are described herein.

For example, active learning uses heuristic scoring strategies to query a small subset of unlabeled examples (which are the most informative within the dataset), and a model is retrained by iteratively adding only a small set of such set selected examples. While this avoids the need to annotate many images, models developed with active learning only apply to test images of the same or identical distributions of the training images. Thus, active learning cannot be used to produce a generalized model suited for the high variability in dyes, scanners, tissues, etc. that exist in digital pathology.

As another example, techniques disclosed herein provide a GUI that is configured to allow a user to very efficiently provide labeling input. While other annotation tools have been developed based on machine learning or deep features, such approaches require pre-trained models on a similar segmentation task to the input images, which significantly limits model generalizability. Further, such approaches are limited to binary segmentation, whereas most applications in digital pathology require simultaneous identification of three or more different types of target regions.

As yet another example, while transfer learning and domain adaptation improve model generalization to a certain extent, they require additional model training with additional labeled examples from the image domain of interest. Although unsupervised domain adaptation aims to use no annotations from the target domain, it still relies on a validation set from the targeting domain for model selection, which inevitably tends to overfit to the validation set. In addition, a prerequisite for these approaches to work well is the existence of similarities between the image domains. Therefore, such approaches provide neither real-time prediction modification, nor cross-domain generalizability without assumptions about image domains or without additional model retraining.

Additionally, many existing segmentation models (both optimization-based and learning-based approaches) are designed to segment individual objects one at a time, which simultaneously identify two different types of regions with binary segmentation: a foreground object and non-target background. A foreground object ("foreground" for short) is defined as a target object instance in an image, while non-target background is anything else besides the target object. Meanwhile embodiments of the present invention result in segmentation of target objects, no matter if it is a single connected region or multiple disconnected regions of a same class.

Exemplary Network for Digital Pathology Image Generation and Processing

Figure 1:
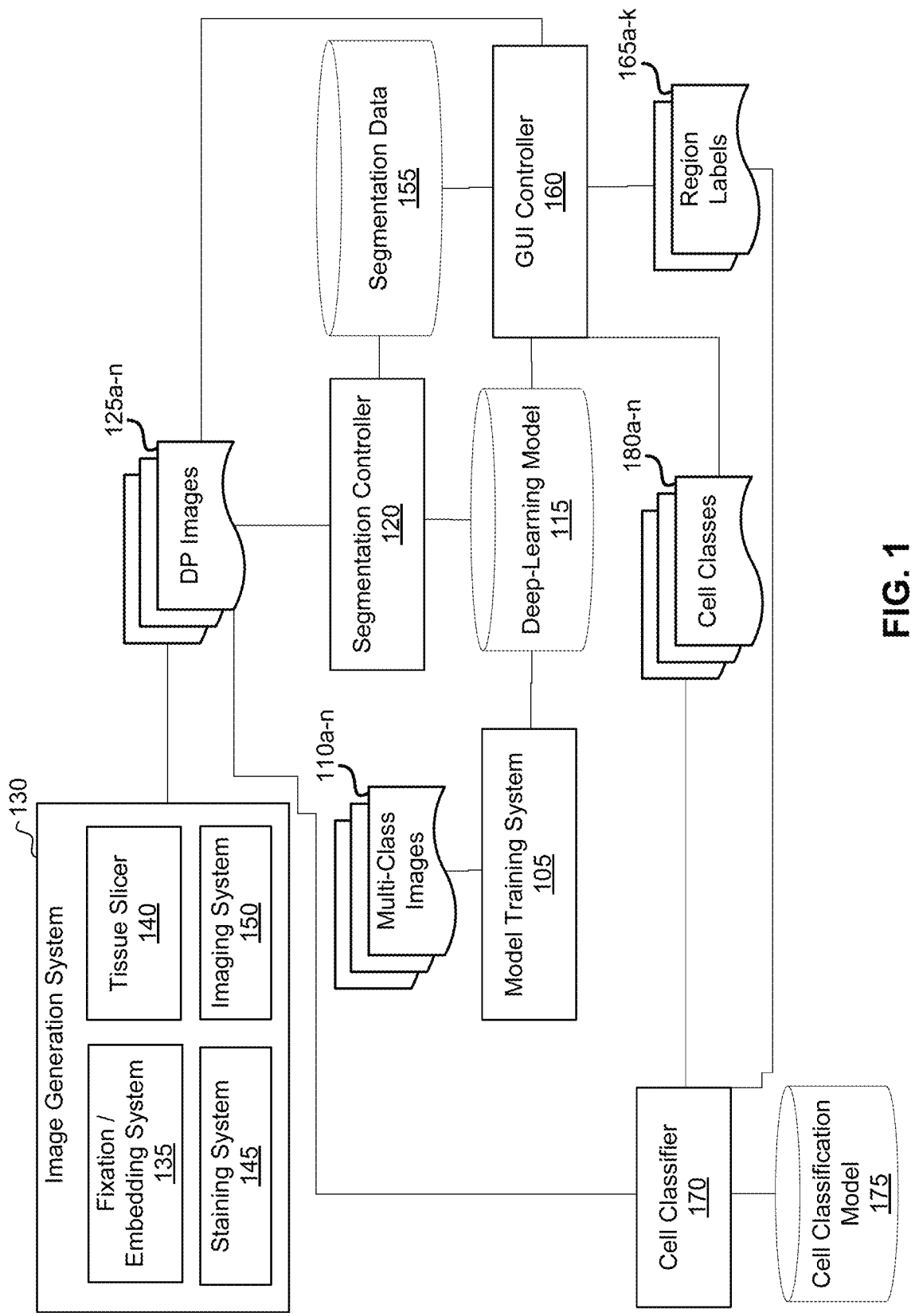
FIG. 1 shows an exemplary network for generating a digital pathology image and detecting and labeling regions within the digital pathology image and for classifying cells in the digital pathology image.

FIG. 1 shows an exemplary network for generating a digital pathology image and detecting and labeling regions within the digital pathology image and for classifying cells in the digital pathology image. It will be appreciated that each of one or more of the depicted components in FIG. 1 (e.g., model training system 105, segmentation controller 120, imaging system 150, GUI controller 160, cell classifier 170, etc.) may include one or more processors and a computer-readable medium with instructions that, when executed, perform actions identified herein. In some instances, a single physical or virtual computing system includes one or more processors and a computer readable medium with instructions that, when executed, perform actions described as being performed by multiple components in FIG. 1. For example, a single computing system may perform actions described herein as being performed by model training system 105, segmentation controller 120, GUI controller 160, and cell classifier 170.

The network includes a model training system 105 that retrieves or retrieves multi-class images 110a-n from one or more data sources. The one or more data sources may include one or more remote data sources and/or one or more local data sources. In some instances, at least some of the multi-class images 110a-n are retrieved by sending an online request for images and downloading images. Each of the multi-class images 110a-n can include annotation data that indicates borders of or areas of depictions of different segments in the image. The segments in each of the multi-class images 110a-n may correspond to different types of objects or things. For example, rather than only identifying where a vehicle is depicted in an image, the annotation data may identify depictions of each vehicle, each stop light, each crosswalk, each person, etc.

The multi-class images 110a-n may, but need not, be from different domains. The multi-class images 110a-n may include (for example) one or more natural-scenes images, one or more digital pathology images, one or more immunohistochemistry images, one or more H&E images, one or more MM images, and/or images from one or more other domains. The multi-class images 110a-n may, but need not, include one or more digital pathology images. The multi-class images 110a-n may include one or more images that are not digital pathology images.

Each of the multi-class images 110a-n may be accompanied by segmentation annotation data. The segmentation annotation data may include annotations as disclosed herein. For example, the segmentation annotation data may include one or more click annotations, each of which correspond to a specific pixel in the image and a specific positive label (e.g., identifying a particular class) of negative label. As another example, the segmentation annotation data map includes a transformed version of one or more click annotations (e.g., where each click annotation was transformed using a map, such as a click map or Euclidean map). As another example, the segmentation annotation data may include one or more ground-truth masks that indicate—for each pixel—an identification or prediction as to whether the pixel corresponds to a particular label. The segmentation annotation data may be identified by or generated based on input from a user interacting with a GUI that shows each training image. It will be appreciated that a user providing input for the segmentation annotation data need not be the same user as one providing a subsequent image (and/or other related information) to be processed by the trained model.

The model training system 105 may use the multi-class images 110a-n (e.g., and any accompanying segmentation annotation data) to train a deep-learning model 115. The deep-learning model 115 may include a neural network with more than three, more than four, more than five, or more than six layers. The deep-learning model 115 may have a convolutional neural network architecture. Training the deep-learning model 115 may include learning the values of a set of learnable parameters (e.g., weights assigned to connections between various nodes) of the model.

After the deep-learning model is trained, a segmentation controller 120 can use the trained deep-learning model to process each of one or more digital-pathology (DP) images 125a-n to identify different (e.g., non-overlapping or overlapping) segments in the image. Each DP image 125 may have been generated by an image generation system 130, which may be remote from or local with segmentation controller 120. It will be appreciated that some actions performed by image generation system 130 (and/or by one or more components thereof) are performed automatically, while others (in some instances) are performed using at least some human action.

As part of the image generation system 130, a fixation/embedding system 135 fixes and/or embeds a tissue sample (e.g., a sample including at least part of at least one tumor) using a fixation agent (e.g., a liquid fixing agent, such as a formaldehyde solution) and/or an embedding substance (e.g., a histological wax, such as a paraffin wax and/or one or more resins, such as styrene or polyethylene). Each slice may be fixed by exposing the slice to a fixing agent for a predefined period of time (e.g., at least 3 hours) and by then dehydrating the slice (e.g., via exposure to an ethanol solution and/or a clearing intermediate agent). The embedding substance can infiltrate the slice when it is in liquid state (e.g., when heated).

A tissue slicer 140 then slices the fixed and/or embedded tissue sample (e.g., a sample of a tumor) to obtain a series of sections, with each section having a thickness of, for example, 4-5 microns. Such sectioning can be performed by first chilling the sample and then slicing then sample in a warm water bath. The tissue can be sliced using (for example) using a vibratome or compresstome.

Because the tissue sections and the cells within them are virtually transparent, preparation of the slides typically includes staining (e.g., automatically staining) the tissue sections in order to render relevant structures more visible. In some instances, the staining is performed manually. In some instances, the staining is performed semi-automatically or automatically using a staining system 145.

The staining can include exposing an individual section of the tissue to one or more different stains (e.g., consecutively or concurrently) to express different characteristics of the tissue. For example, each section may be exposed to a predefined volume of a staining agent for a predefined period of time. The stain may be configured to be absorbed by (for example) a cell membrane target, a nuclear target, a cytoplasmic target, an intracellular-component target, or an extracellular-component target.

One exemplary type of tissue staining is histochemical staining, which uses one or more chemical dyes (e.g., acidic dyes, basic dyes) to stain tissue structures. Histochemical staining may be used to indicate general aspects of tissue morphology and/or cell microanatomy (e.g., to distinguish cell nuclei from cytoplasm, to indicate lipid droplets, etc.). One example of a histochemical stain is hematoxylin and eosin (H&E). Other examples of histochemical stains include trichrome stains (e.g., Masson's Trichrome), Periodic Acid-Schiff (PAS), silver stains, and iron stains. The molecular weight of a histochemical staining reagent (e.g., dye) is typically about 500 kilodaltons (kD) or less, although some histochemical staining reagents (e.g., Alcian Blue, phosphomolybdic acid (PMA)) may have molecular weights of up to two or three thousand kD. One case of a high-molecular-weight histochemical staining reagent is alpha-amylase (about 55 kD), which may be used to indicate glycogen.

Another type of tissue staining is immunohistochemistry (IHC, also called "immunostaining"), which uses a primary antibody that binds specifically to the target antigen of interest (also called a biomarker). IHC may be direct or indirect. In direct IHC, the primary antibody is directly conjugated to a label (e.g., a chromophore or fluorophore). In indirect IHC, the primary antibody is first bound to the target antigen, and then a secondary antibody that is conjugated with a label (e.g., a chromophore or fluorophore) is bound to the primary antibody. The molecular weights of IHC reagents are much higher than those of histochemical staining reagents, as the antibodies have molecular weights of about 150 kD or more.

The sections may then be individually mounted on corresponding slides, which an imaging system 150 can then scan or image to generate raw digital-pathology images 125a-n. Each section may be mounted on a slide, which is then scanned to create a digital image that may be subsequently examined by digital pathology image analysis and/or interpreted by a human pathologist (e.g., using image viewer software).

A GUI controller 160 can generate, configure or update a GUI to present a given digital-pathology image that is associated with a user. The given digital pathology image may be one queued for segmentation and label processing or one that has been identified in a request for segmentation and label processing. The GUI may be configured to receive one or more annotations. For example, the GUI may include input components that allow a user to select a set of pixels in the digital pathology image and to indicate—for each of the set of pixels—a label that is (or is not) to be assigned to the pixel (e.g., a first type of region, a second type of region or background).

The segmentation controller 120 can process each digital-pathology image 125a-n and any annotations using the trained deep-learning model 115 to generate segmentation data 155. The segmentation data identifies—for each segment detected by the deep-learning model 115—where the segment is within the corresponding digital-pathology image 125. For example, for a given segmented region, the segmentation data 155 may identify pixels that are in a border of the region and/or pixels that are in the segmented region. In some instances, segmentation data 155 includes an annotation image that indicates—for each of one or more pixels—whether the pixel has been assigned to a type of region or a segmented region and, if so, which one. For example, the annotation image may indicate to which of a predefined set of classes (e.g., a first type of region, a second type of region, or background) a pixel has been assigned. Though the classes may lack semantic meaning, the training may be performed such that any class assignment is likely to be consistent with any annotations provided with the respective digital pathology images 125*a-n*. As another example, each segmented region may be assigned an identifier that is unique relative to other segmented regions in the image. For each segmented region, the pixels that are within the segmented region (or, alternatively or additionally, are part of a boundary of the segmented region) can be assigned a value equal to the unique identifier.

A GUI controller 160 can generate, configure or update a GUI to present a given digital-pathology image (e.g., at a reduced intensity) and to show the boundaries of each segmented portion. When the deep-learning model is configured to assign labels, the labels may also be represented (e.g., via a shading, color of a background, color of a symbol, etc.).

The GUI can also be configured to receive input that identifies or updates a region label for each region. The GUI may be configured to allow a user to zoom in and out of the image and/or to move the field of view. This can allow the user to better see details, such as the morphologies and sizes of cells within a given segmented region.

The GUI may be configured such that, for each segmented region, a user can select from among a predefined set of region labels. When label data was provided as part of the training data, the deep-learning model may have generated a predicted class for each region. In that case, an indication of the predicted class may be presented for each segmented region (e.g., via a shading, background color, symbol color, symbol shape, etc.). When label data was not provided as part of the training data (or when insufficient label data was provided), all regions may be represented as having an indication that a region label has yet to be assigned, though a region label may be subsequently assigned to each segmented region (and the representation may be updated accordingly) based on label-selection input provided by a user. In other instances, an initial region label is automatically assigned to each region, and a user may selectively provide input to change the label when the user believes that the initial label was incorrect. In this case, all regions may be assigned a same initial region label (e.g., a label that is statistically most common), or one or more rules may be evaluated to determine which initial region label to assign to each region (e.g., based on an area of the region, a perimeter of the region, a perimeter-to-area ratio of the region, a number of cells detected within the region, etc.).

In any case, the GUI may be configured to receive input that identifies (e.g., as an initial indication or as an update indication) a label that is to be assigned to one or more portions of the image. For example, a user may click on a marker that is color coded to use a radio-button list to identify an initial labeling and may then provide input that identifies a different label. As another example, a user may click within a segmentation region depiction and may then use a defined mouse click signature so as to identify an initial (e.g., and final) label) for the region.

In some instances, a distinct type of mouse click and/or touchscreen interaction may be assigned to each of the predefined set of region labels. For example, each of: (1) a single left mouse click; (2) a single right mouse click; and (3) a double left mouse click can be assigned to one of the region-label options. (FIG. 7 and the associated descriptions provide an illustration of a mapping of mouse clicks to labels.) As another example, each of (1) short hold and then swipe down slightly; (2) short hold and then swipe up slightly; and (3) short hold and then swipe left slightly may be assigned to one of the region-label options.

The GUI may also include an option to (for example) assign any and/or all currently unlabeled segmentation regions in an image or all currently unlabeled segmentation regions fully in a field of view to a given region label (which may be selected by the user). Thus, for example, within a given field of view, the user may then choose to label all stroma and background regions and to then indicate that all other regions are to be labeled as tumor regions. The GUI may alternatively or additionally be configured such that a user can select a tool to define a rectangular area in a depicted image and then to assign all regions within the area to a selected region label.

As each label is assigned or updated, the GUI may be updated to reflect the label (e.g., by adding a background color, which may represent the assigned label, to the region), such that the user can easily see the current labels (and, if applicable, which regions remain unlabeled). The GUI may include a submit or completion input option that can be selected by the user when the user is satisfied with the labels. Further details of the GUI are provided herein, such as when describing FIG. 8.

GUI controller 160 may store and/or output region region labels 160*a-k*. The region labels 160*a-k* may (for example) include a mapping that associates each unique region identifier with a region label (or region-label identifier). The region labels 160*a-k* may alternatively or additionally include a mapping that associates, for each of some or all pixels in the image, the pixel with a region label (or region-label identifier). The region labels may be used (for example) to generate training data to train another machine-learning model to detect and/or classify cells depicted in digital pathology images.

The region labels may further or alternatively be used (for example) to facilitate performing digital pathology analyses that include characterizing cells depicted in the images. A cell classifier 170 may use a classification model 175 to process the digital-pathology image to detect and classify each depicted cell so as to identify cell classes 180*a-n*. The classification model 175 can be (for example) a machine-learning model, a neural network, a deep neural network, and/or a convolutional neural network. In some instances, the classification model 175 is part or all of the HALO model. In some instances, the cell classes 180*a-n* were determined using region segmentations that are different from segmentation 155 (e.g., using a region segmentation performed by the HALO model).

Each of the cell classes 180*a-n* may indicate whether each of multiple stains were detected as having been absorbed for a given cell. For example, in a duplex scenario with two stains, there may—at least initially—be four unique cell classifications.

In some instances, cell classifier 170 assesses consistency between the cell classifications and the region labels 165*a-k*. For example, cell classifier 170 can determine whether any cells are within a region labeled as a background region. If any such cells were assigned cell classifications representing that they do or do not have each of one or more biomarkers, the classifications may impede statistical calculations. For example, even if the cells were assigned to a classification that indicates that the cells do not include either of two biomarkers of interest, the cells may then still contribute to a total cell count that is used as a normalization. Thus, for example, a statistic that identifies a portion of cells having a given biomarker may be calculated as being a portion that is lower than it is in reality in this circumstance. As another example, if a given background region corresponds to a tissue fold or blur, the noise of the signals may be high such that considering any cell classifications from these regions may decrease the accuracy and reliability of a statistic.

Thus, in some instances, cell classifier 170 automatically changes the classification of each cell in a background region to a new background cell-classification label. The background cell classification may indicate that data pertaining to the cell is not to be used when generating metrics about the slide or sample. For example, a total cell count may be configured to not include cells having the background cell classification.

In some instances, instead of cell classifier 170 detecting inconsistencies and automatically updating select cell classifications, GUI controller 170 is configured to detect the inconsistencies. GUI controller 170 can then avail an interface to a user that indicates such consistencies and provides a tool configured to receive input corresponding to an instruction to change a label for a cell classification or for a region. The GUI may represent a region label by using (for example) a shading or color and a legend. The GUI may represent a cell-classification label by using a marker color or shape.

The GUI can be configured to receive input indicating that a cell classification is to be changed to a background cell classification (even if no such classification was presented in the initial cell classes 180a-n generated by cell classifier 170). The GUI may be configured such that a user can individually select a representation of a single cell or may select multiple cell representations (e.g., by using a rectangular select tool, a free-form select tool, or by pressing a shift or control key while clicking on multiple cell representations). The user may then identify a cell classification to be applied to the cell(s).

Exemplary Interactive Segmentation Workflows

Figure 2:
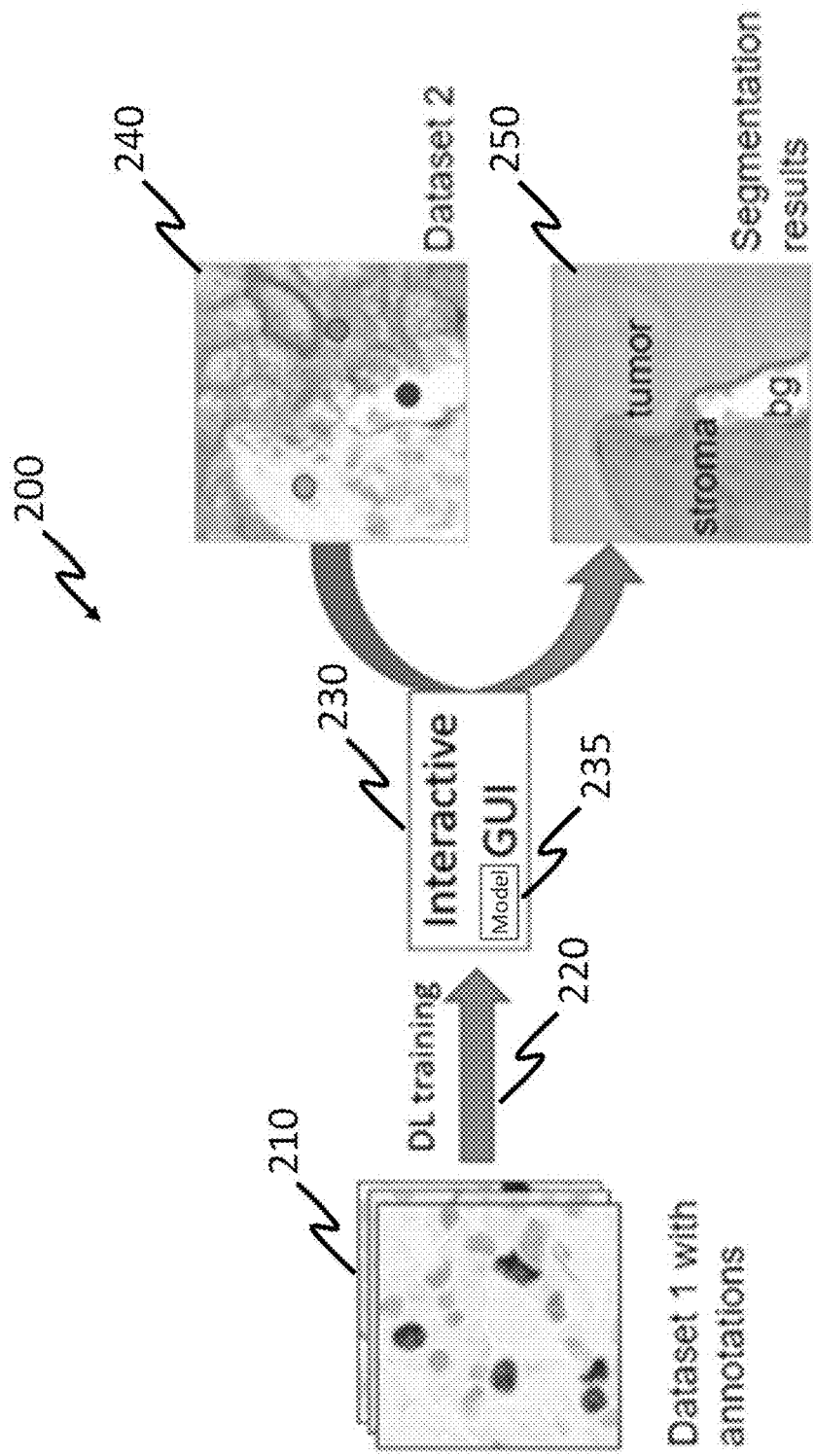
FIG. 2 depicts an embodiment of the multi-class DL-based interactive segmentation workflow.
Figure 3:
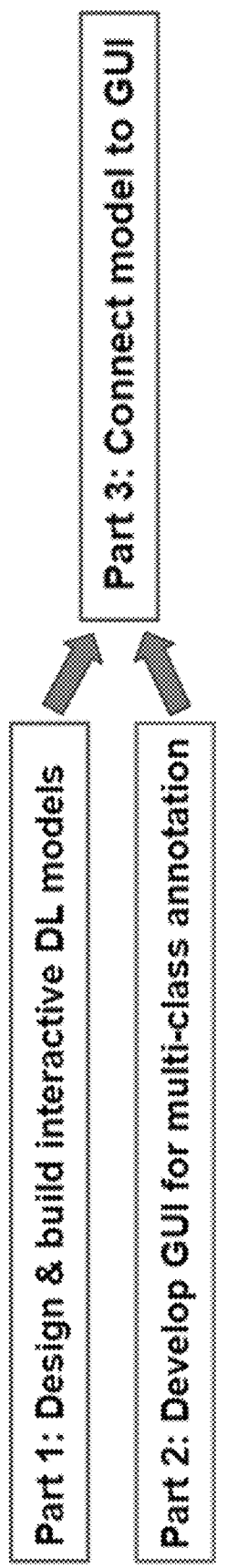
FIG. 3 depicts an embodiment of applying interactive binary segmentation to multi-class segmentation of a DP image.

Referring to FIG. 2, an embodiment of a multi-class interactive segmentation workflow 200 is depicted. Various actions in the multi-class interaction segmentation workflow 200 may be performed by model training system 105, segmentation controller 120 and/or label GUI controller 160. FIG. 3 depicts an example of a corresponding pipeline for model building is depicted according to various embodiments.

In various embodiments, the multi-class interaction segmentation workflow 200 designs and builds a deep learning model to perform segmentation on multiple classes and to receive user input that identifies a label for each of one or more pixels and/or segmented region. An interactive GUI may be configured to receive an input image and to potentially initially receive annotation input that identifies a class to which a given point or segment is to be assigned and/or to receive post-training input that identifies or updates a label to be assigned to a given segmented region.

For example, a first dataset 210 may include a plurality of images (e.g., multi-class images 110a-n) from one or more classes (e.g., DP images, natural scene images, immunohistochemistry images, H&E images, or any other relevant images) and may include corresponding annotations (e.g., that identify click annotations, distinct segments within the images, a ground-truth map, etc.). Part or all of the first dataset 210 may have been received via an interactive GUI from a user that is facilitating training a deep-learning model (e.g., deep-learning model 115) that is connected with the interactive GUI.

The plurality of images may include digital pathology images featuring different tissue types and their corresponding segmentation annotations. In other embodiments, the first dataset 210 from another domain, for example, natural scene images may be used. The first dataset 210 may include (for example) annotation data that associates each of one or more pixels or areas with a given class. The class may be one of multiple predefined non-semantic classes.

The deep-learning model may have been designed and built (at part 1 of FIG. 3) by defining the model's architecture, hyperparameters, and loss function. At 220, the first dataset 210 may be utilized (e.g., by model training system 105) to train the deep-learning model. By using datasets from multiple domains, the resulting model that is trained using the data may be more generalizable as compared to using training data from a single domain.

A GUI can also be developed that is configured to display a digital pathology image and segmentation data (e.g., by overlaying segmentation boundaries on the image) and to receive user inputs that identify a label (e.g., of a predefined set of labels) for each section or to correct a predicted label. (See Part 2 of the pipeline of FIG. 3.) This interactive GUI may be, but need not be, a GUI that received part or all of the first dataset. Even if the GUI is the same, the GUI may be configured to present a first interface for receiving part or all of the first dataset to a first user and to present a second interface for receiving label definitions or updates to a second user.

The GUI of part 2 may be connected to the model (see part 3 of the pipeline of FIG. 3). This connection can allow a user to identify (e.g., upload, select, etc.) one or more digital pathology images and/or checkpoint annotation data (e.g., a second dataset of images) and request processing via the GUI. The request can automatically trigger processing by the deep-learning model to identify segmentation, and—once the segmentations are identified—the GUI can automatically display the image and segmentation data and be configured to receive label identifications or updates. In some embodiments, an initial label (e.g., a non-semantic label) may be assigned to each of one or more segmented regions. In some embodiments, at least one segmented region lacks an initial label.

Using an interactive GUI 230 (e.g., controlled by label GUI controller 160), the user may efficiently identify and/or update labels for at least some of the segmented regions. For example, in various embodiments, the user may use a mouse and click on areas to provide annotations. The interface may be configured such that annotations (e.g., identifying new or updated labels) can be made quickly and efficiently and such that the GUI is updated in real-time so as to reflect the most recent labels for the regions. For example, in various embodiments, different colors may be used to annotate different classes. For example, a blue dot may be used to annotate a stroma region, a green dot to annotate a tumor region, and a red dot to annotate a background region. Furthermore, multiple annotations may be used for one or more of the classes.

In various embodiments, the trained deep-learning model 235 is not further modified after the initial training (using the multi-class data). Instead, the deep-learning model 235 outputs segmentations for an image, and the interactive GUI is configured to receive inputs that quickly identify labels for each of some of all of the segmented regions.

In one embodiment, the deep-learning model is used to segment an image tile of 600×600 pixels in less than a minute. Thus, a user may quickly and efficiently annotate an image or perform image segmentation. Further, with no model retraining or fine-tuning required during use, the model does not over-fit to specific datasets and maintains generalizability. In addition, the system provides confidence to users because the process and outputs are not a black-box, such a traditional deep-learning system and instead enables user-guided modifications of model prediction, which provides real-time feedback and thus is interactive, intuitive, and flexible for end-users.

Exemplary Segmentation Approach Using Limited Annotation

Figure 4:
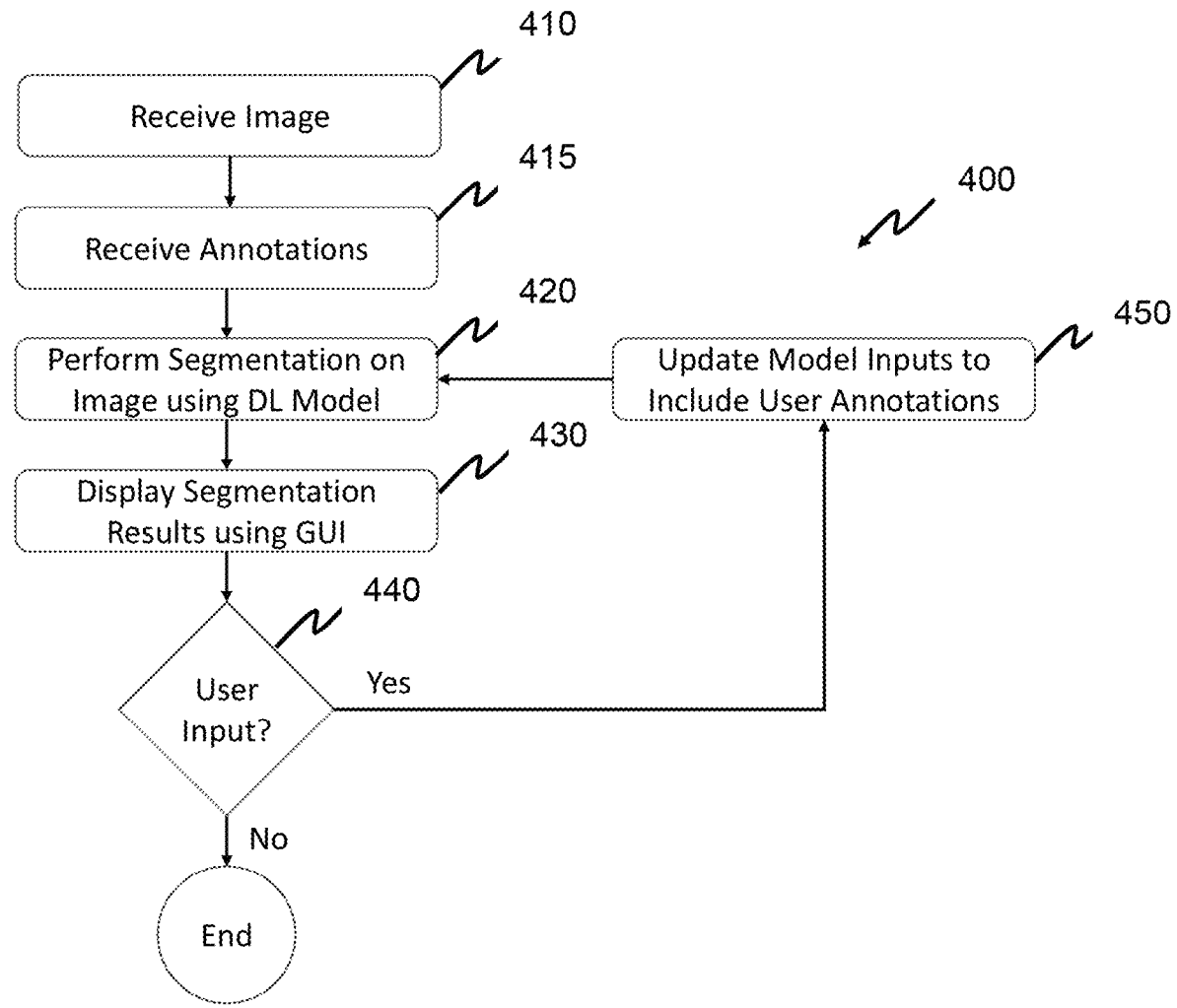
FIG. 4 depicts an example of a pipeline for model building according to various embodiments.

Referring to FIG. 4, an exemplary process 400 of an interactive segmenting is depicted. In various embodiments, the multiclass deep learning system receives an image to be segmented (Step 410). In some embodiments, the image may be a complete image (e.g., a whole slide digital pathology image) or a portion of an image (e.g., a field of view of a complete image, a region of interest of a complete image, a tile of a complete image, etc.). In various embodiments, the user may provide one or more annotations for the image (Step 415). Such annotations may include (for example) click annotations, which may potentially be further processed to be transformed to other annotations using a transformation algorithm. In various other embodiments, no annotations may be provided by the user before the initial segmentation.

Segmentation may be performed on the image (and its annotations, if available) using the deep learning model (Step 420). In various embodiments, the model may be an n-class model. Thus, the model may be configured to segment the input image in up to n types of different areas in each round of user interaction, which generates a single segmentation mask with up to n classes of areas. For example, in various embodiments, the deep learning model is a three-class model configured to classify the input image into areas including tumor cells, stroma cells, and background tissue. In other embodiments, the deep learning model is a four-class model configured to classify the input image into four different areas including immune cells, tumor cells, stroma cells, and background cells. It should be understood by those skilled in the art that the deep learning model can be configured for any number of classes and to segment any type of tissues or cells.

The deep learning model output provides a segmented image to the interactive GUI and the results are displayed to the user (Step 430). The user may then elect to provide annotations using the interactive GUI (Step 440). When the user provides annotations, the interactive GUI provides the annotations to the deep learning model as additional inputs (Step 450) and the process may be repeated as many times as are required to achieve satisfactory results.

EXAMPLES

Example 1

Traditional interactive segmentation models, both optimization-based and learning-based algorithms, are designed to segment individual objects one at a time, which simultaneously identify two different types of regions with binary segmentation: a foreground object and non-target background. A foreground object ("foreground" for short) is defined as a target object instance in an image, while non-target background is anything else besides the target object.

Techniques disclosed herein can generate strong results where the targeting objects can be segmented with reasonable success, no matter if it is a single connected region or multiple disconnected regions of a same class. An interactive binary segmentation was used for multi-class segmentation of a DP image.

Figure 5:
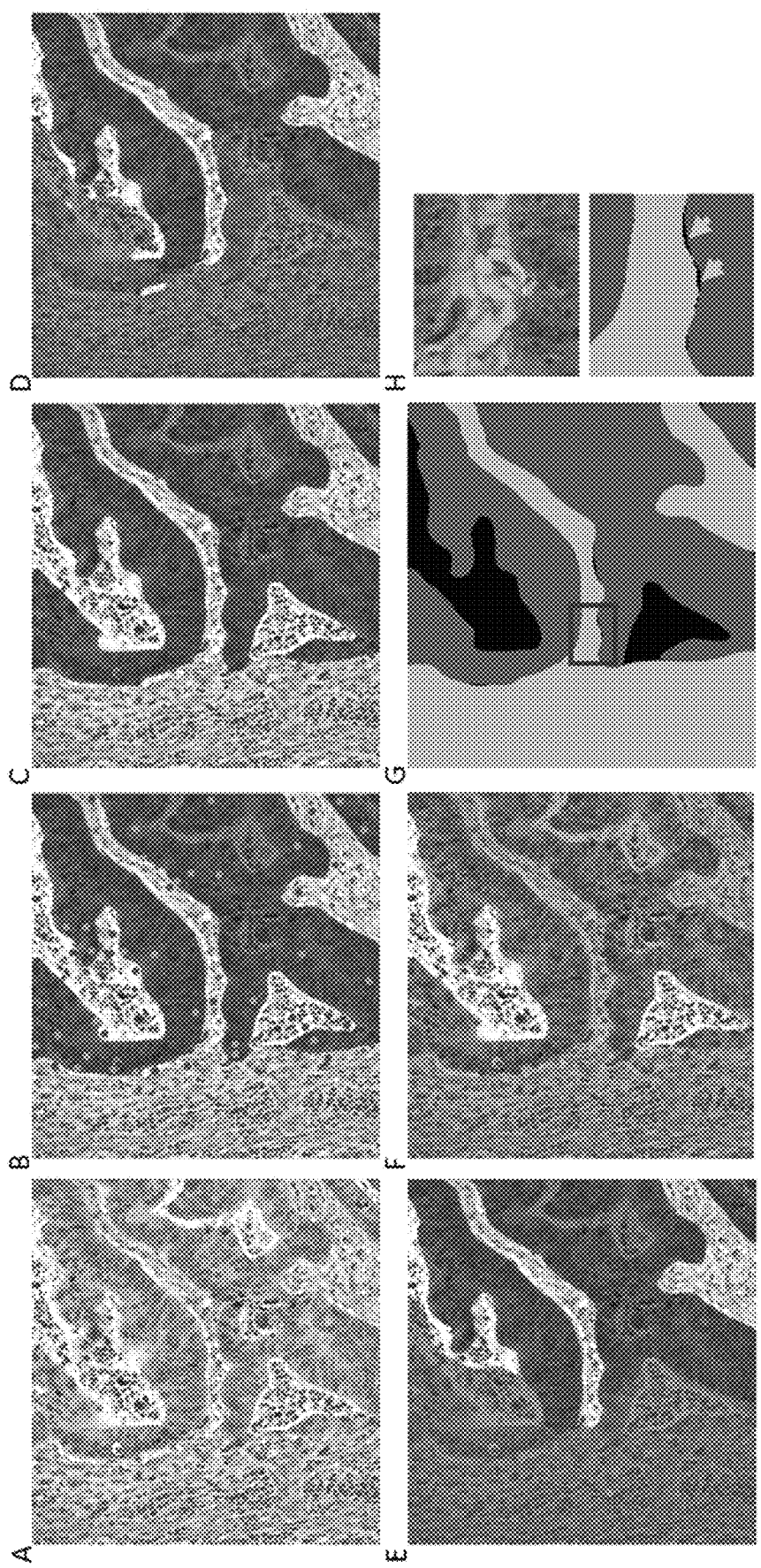
FIG. 5 depicts an example workflow of the multi-class deep learning system according to various embodiments.

FIGS. 5A-5H illustrate the steps performed when binary segmentation is used to segment a digital pathology image to identify three types of regions. FIG. 5A shows an exemplary colon cancer H&E image tile. FIG. 5B shows a first round of binary segmentation to identify tumor (red masked regions) and non-tumor (rest of non-masked regions). FIG. 5B depicts the same image tile after a first round of binary segmentation was performed using the deep learning model to identify tumor (red masked regions) and non-tumor (rest of non-masked region). In this example, a user has annotated the image using the interactive GUI 130 with green dots using positive clicks on tumor regions and red dots using negative clicks on non-tumor regions. FIG. 5C shows an example of an updated tumor region segmentation result (red masked regions). Thus, the tumor regions are identified despite being disconnected in this image.

FIG. 5D depicts the image after a second round of segmentation that identifies stroma and non-stroma regions. At this point, a green dot indicates a first positive click to identify the stroma region. The green masked regions are stroma regions identified in the second round of segmentation after the first positive green click, and the red masked regions are tumor regions identified by the first round of segmentation of tumor versus non-tumor regions. In the depicted example, after the first green click, the prediction of the stroma region extends to the previously identified tumor region, due to the second round of segmentation being completely independent of the first round.

FIG. 5E depicts an example of correcting stroma segmentation results where a red dot (negative click) has been added. FIG. 5F depicts a series of click annotations that modify the second round of segmentation. FIG. 5G depicts the final segmentation result for tumor, stroma and background regions where light blue corresponds to stroma regions, gray corresponds to tumor regions, and black corresponds to background regions. FIG. 5H depicts zoomed-in views from the red rectangle region from FIG. 5G. The upper image includes segmentation results overlaid on the original image and the lower image shows the segmentation mask that was used. In this example, the arrows point to gaps after combining masks generated from two rounds of segmentation.

Since each round of binary segmentation is independent, users need to make corrections for the already segmented objects from previous rounds (FIGS. 5D-5E). This prolongs the analysis time because of the corrections needed for the previously identified regions in addition to the targeting classes in the current round of segmentation (FIG. 5F). Such corrections to remedy the already annotated regions is redundant and time-consuming. In addition, users need to carefully provide click annotations via clicks at the boundaries of the targeting classes, otherwise gaps often occur between segmented objects (FIGS. 5G-H) from different rounds of segmentation and thus inevitably leading to confusions and errors.

Example 2

Figure 6:
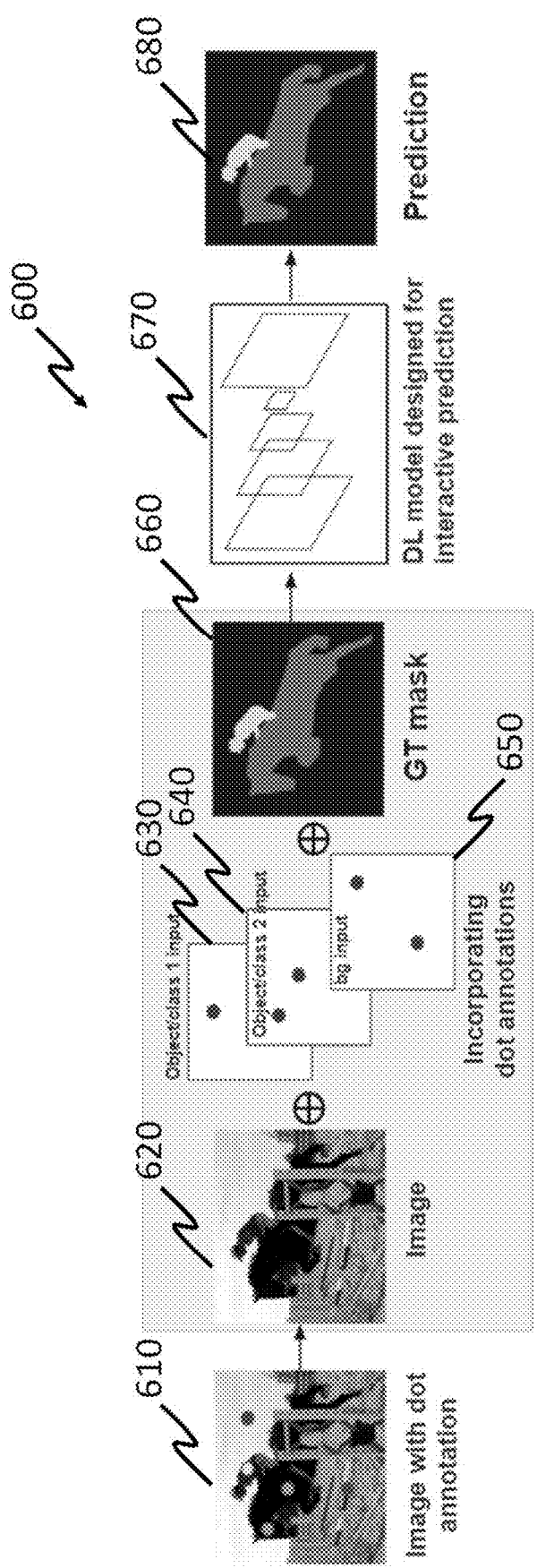
FIG. 6 depicts an embodiment of a three-class deep learning model and training.

FIG. 6 shows an exemplary representation of the use of a three-class deep learning model 600. For a three-class model, the ground truth masks contain up to three different types of regions, and user annotations contain up to three sets of user annotations, with each corresponding to one type of region.

The ground truth masks for each segmentation task are instance-level annotations where multiple object instances are annotated. For example, during training, up to two objects are sampled from a mask to generate a new mask, where the rest of the image is regarded as non-target background. Such non-target background can contain (a) other objects that are not selected from the original mask, and (b) pure background, where no objects are annotated in the original mask.

Training data for the three-class deep learning model includes an image with click annotations 610. Colored dots represent the mouse clicks on targeted regions. The location and number of dots are simulated for model training, to mimic user inputs at test time, where a user provides mouse clicks to guide the segmentation of targeting regions.

Simulated click annotations are used during training. For example, mouse clicks annotations are encoded into disk maps or Euclidean distance maps, which form additional masks that can be conveniently fed into a deep learning model together with a training image. Various strategies of click simulation may be utilized for binary interactive segmentation, including positive click sampling and negative click sampling. Positive click sampling mimics users' behaviors of mouse clicking on a target object by sampling a variable number of pixel locations randomly within the target object region in the mask. Negative click sampling mimics users' behaviors for identifying background (i.e., anywhere not on the target object). In various embodiments, three strategies of negative click sampling may be used. For example, a first strategy may include using a variable number of pixel locations that are randomly sampled from the pure background regions. A second strategy may include using a variable number of pixel locations sampled from unselected objects in the ground-truth masks. A third strategy may include using a variable number of pixel locations from the pure background that are sampled close to the boundaries of the target object.

In this Example, to train a three-class deep learning model, negative click sampling is used for one type of region and positive click sampling for the other two types of regions. It will be appreciated that negative clicks may be better for effectively correcting erroneously segmented regions. Thus, keeping such negative click sampling for one of the classes provides the flexibility for users to perform negative clicks for the class of the region that is most difficult to segment.

The image with annotations 610 is split into an image 620 and annotations for each object/class being segmented by the deep learning model 600. For example, the three-class deep learning model includes a first class annotation input 630, a second class annotation input 640, and a background annotation input 650. The image 620 and the annotations 630, 640, 650 are then used to generate a ground truth mask 660, which is used to train the deep learning model 670 which can then generate the prediction 680.

Example 3

Figure 7:
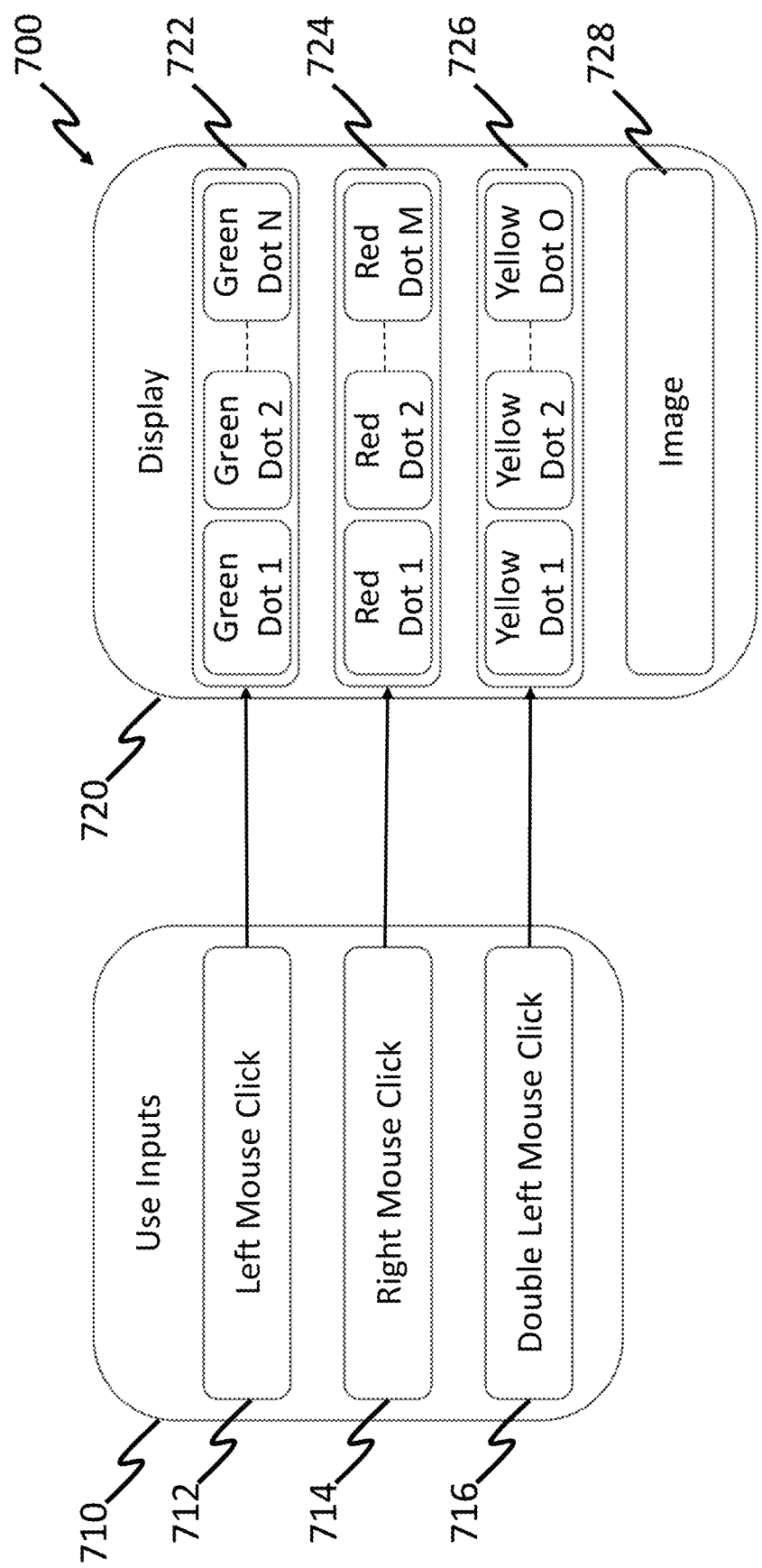
FIG. 7 depicts an example workflow of providing annotations according to various embodiments.

FIG. 7 depicts an example workflow of providing annotations via an interactive GUI configured to provide user-input functionality for multiple segmentation classes. Annotations are provided by the user using various user inputs 710 and the GUI is generated on a display 720. The user inputs 710 may include any computer input device such as a mouse, a touch screen, a keyboard or other input device. The user inputs 710 include a mouse with at least two buttons that include a left click button and a right click button.

In a typical binary object segmentation GUI, left mouse clicks are used as positive clicks (i.e., a location is part of a class) and right mouse click as negative clicks (i.e., a location is not part of a class). Using a multi-class interactive GUI, left and right click buttons may be mapped to a class. For example, in a three class system, a left mouse click 712 may be associated with a first class, a right mouse click 714 may be associated with a second class, and a combination mouse click 716 may be associated with a third class. Each of the mouse clicks may cause the interactive GUI to overlay a dot corresponding to the class associated with the click onto the image 728.

A left mouse click 712 may be associated with a first type of region (e.g., a tumor region), and each left mouse click triggers the display of a green dot 722 on the interactive GUI via the display 720. The left mouse click 712 may serve as a positive click. A right mouse click 714 may be associated with a second type of region (e.g., a stroma region) and each right mouse click triggers the display of a red dot 724 by the GUI, and may also serve as a positive click. A double-left mouse click 716 may be associated with the third type of region and may produce a yellow dot 726. In various embodiments, the double-left mouse click 716 may serve as a negative click. To connect a trained model to the interactive GUI, the GUI backend is configured to convert the user clicked pixel locations for three classes to three disk maps and to use these disk maps along with the image as deep learning model inputs for generating predictions for the corresponding three-classes.

Using the interactive GUI, a user may initiate segmentation by adding a first positive click on a target region of interest. This click triggers an initial network prediction. Adding additional clicks triggers the changes of network input, which leads to corresponding changes in the segmentation prediction. The segmentation results can be displayed as a colored overlay on the input image.

Example 4

Figure 8:
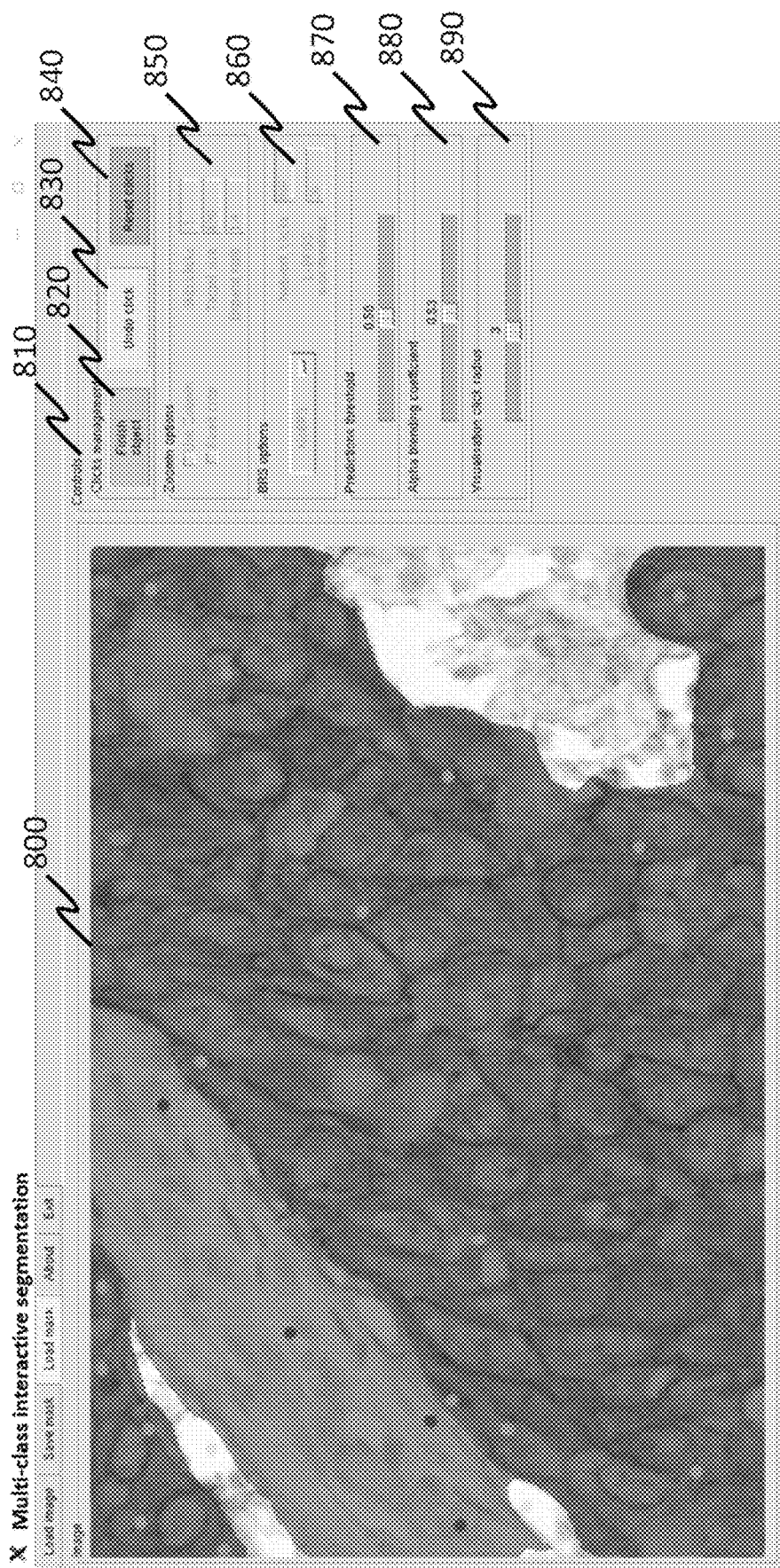
FIG. 8 depicts an example interactive GUI according to various embodiments.

FIG. 8 depicts an example of an interactive GUI for defining click annotations. The interactive GUI includes an image display area 800 and a control panel 810. The image display area 800 is configured to show the image being segmented and provides an area for users to add annotations. The controls allow for a variety of options for operating the system. For example, the interactive GUI may include buttons to finish 820, undo click 830, and reset clicks 840. The GUI controls 810 may also include various zoom options 850. In various embodiments, the user may be able to use the GUI controls to adjust various model parameters. For example, the GUI controls 810 may include back propagation refinement (BRS) options 860, and sliders to modify a prediction threshold 870 and alpha blending coefficient 880. Other control options include a slider for dot radius 890.

Example 5

A title by tile approach is used for whole-slide image segmentation. Tile by tile prediction for WSI. With a tile-by-tile approach, a user performs interactive segmentation one image tile at a time. In this way, a user segments one tile to their satisfaction in the manner described above and then moves on to the next. A platform of interest (web application, GUI, etc.) is chosen to display the whole-slide image and support interactive segmentation. Once all tiles are segmented, the platform can then automatically assemble all predictions and display whole-slide segmentation results.

Example 6

Figure 9:
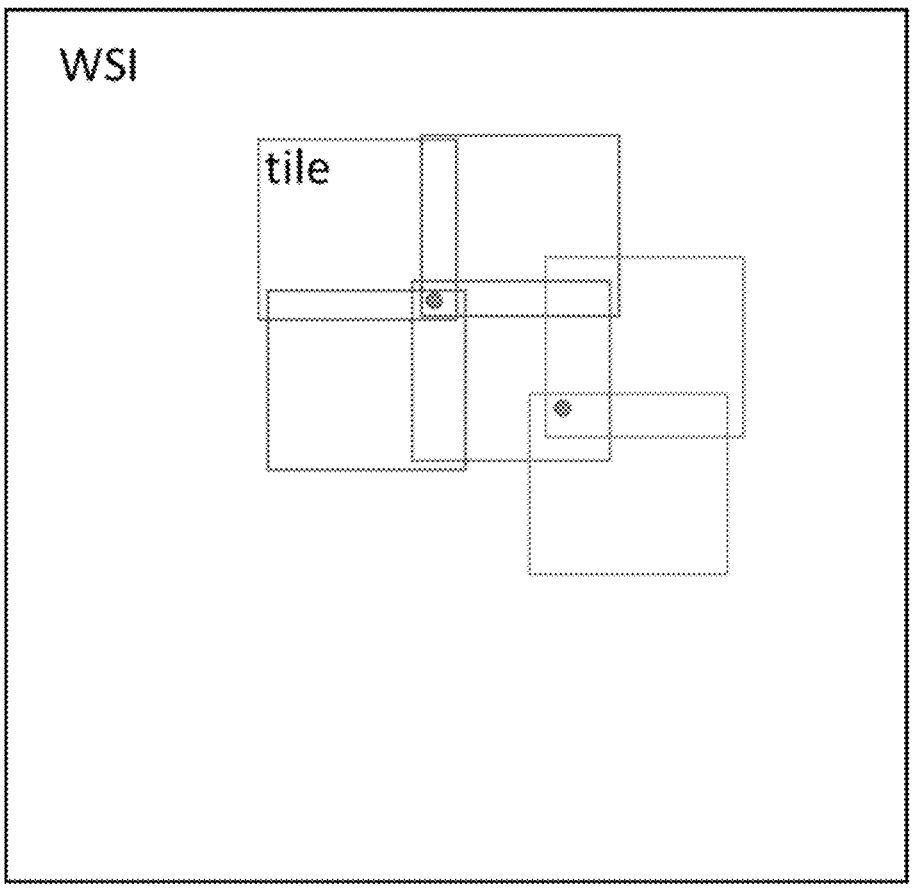
FIG. 9 depicts a visualization of a radial expansion strategy for whole-slide interactive segmentation according to various embodiments.

A radial expansion scheme was used for whole-slide image segmentation. FIG. 8 depicts a visualization of a radial expansion strategy for whole-slide interactive segmentation according to various embodiments. The radial expansion approach leverages the benefit of prediction in overlapping tiles to expand prediction in a radial manner and thus expedite segmentation in a large image like WSI (FIG. 9). For example, when a user starts analysis by clicking anywhere in a WSI (for example, the blue dot in FIG. 9), multiple tiles that cover this click are selected to maximize the total tile coverage, so that predictions for all these tiles can be generated (blue tiles in FIG. 9). In the next step, a user can click anywhere in predicted regions that need to be corrected (example second click shown as orange dot in FIG. 9). The correcting clicks help expand prediction to tiles that cover these clicks (orange tiles in FIG. 9). Since one user click triggers segmentation in multiple tiles, performing such prediction with the designed radial expansion scheme enables much faster propagation of segmented regions in the whole-slide imaging, and thus expedited whole-slide image segmentation. As another advantage of this approach, the system can leverage parallelized or distributed model inference of multiple tiles to further expedite whole-slide image segmentation.

Example 7

Domain-specific and dataset-specific whole-slide image segmentation is provided. In use cases where segmentation is needed for a specific dataset with multiple whole-slide images, interactive segmentation can serve both as an initial annotation-generation strategy and fast annotation expansion strategy. For example, first, a subset of slide image regions can be selected either manually, randomly, or via active-learning-based approaches. Then, segmentation masks of these selected large image regions in selected WSIs can be generated efficiently with one of the aforementioned approaches (i.e., tile by tile prediction or radial expansion strategy), which is then followed by iterative model training and fine-tuning. In this way a model can be quickly built for WSI segmentation of a dataset of interest.

Example 8

A deep-learning model was trained on the Semantic Boundaries Dataset (SBD), a commonly used benchmark for interactive segmentation with instance-level annotations from the natural scene image domain. SBD contains 11355 images, among which 8498 were used for training and 2857 for validation. In each image, one or multiple foreground objects (i.e. instances) are annotated.

An HRNet with OCR modules was pre-trained on ImageNet as a backbone, whose architecture was recently proposed to enable the identification of fine details in a number of vision tasks, including image segmentation and human pose estimation. To incorporate simulated user clicks into model training, convolutional blocks were separately encoded for images and for disk maps from user inputs. Note that such a backbone can be replaced with another model of choice to accommodate specific use cases. In addition, domain-specific annotated datasets, for example, IHC images with corresponding masks, if available, can be utilized to train such an interactive system.

Implementation details: Three-class click sampling was performed on the fly during training. Specifically, for each image, at most two foreground instances (i.e., individual connected objects in ground-truth masks) were selected randomly from the segmentation mask. Together with pure background annotation, a new mask with at most three different regions was generated. Two of the regions correspond to targeting objects, and one corresponds to a non-target background. From such a new mask, positive clicks were randomly placed inside each foreground object region, while negative clicks were placed in the background regions with the same strategies. Images were cropped into 320×480 patches for training and augmented with random rescaling, flipping and color jittering.

Figure 10:
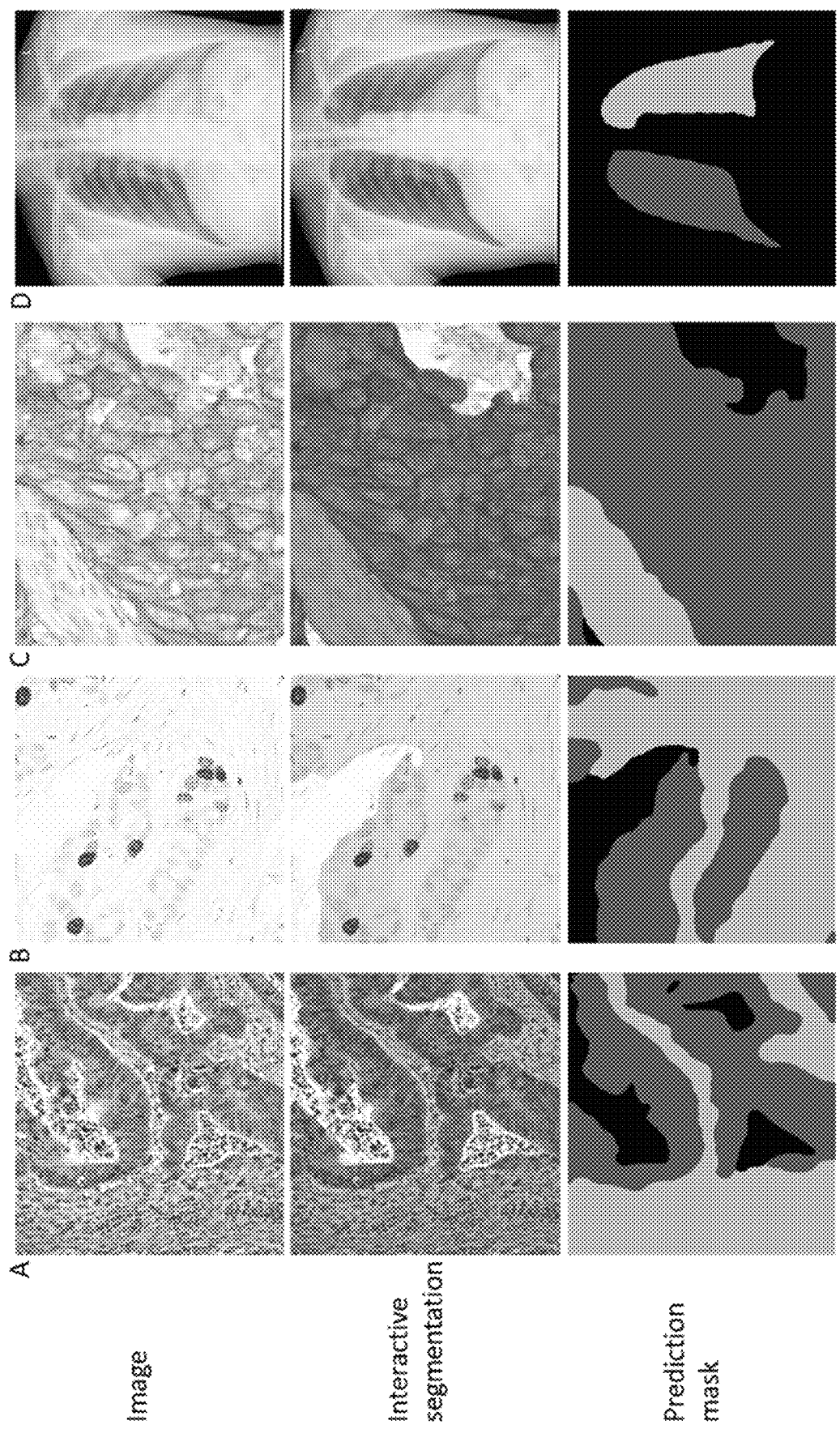
FIG. 10 depicts visualizations of interactive segmentation results from four image domains according to various embodiments.

The interactive platform was used to segment images of four different classes, as shown in FIG. 10. Specifically, FIG. 10 depicts images that include (A) Model performance on an example colon cancer H&E image tile (B) Model performance on an example IHC image from breast cancer tissue targeting Ki67 (brown DAB stain) and counterstained with hematoxylin (blue stain), (C) an example IHC image from lung cancer tissue targeting PDL1 (pink Tambra stain) and CK7 (yellow Dabsyl stain) with hematoxylin counterstain (blue), and (D) an example chest X-ray image. In the bottom panel of A-C, light blue regions are stroma, gray regions are tumors and black regions are non-target backgrounds. In the bottom panel of D, the light blue region is the right lung, the gray region is the left lung and the black region is the non-target background. The predictions demonstrate that the proposed model design and training strategies successfully segment images for three classes of regions interactively, as demonstrated in FIG. 10.

Example 9

HALO Cell Classification

Figure 11:
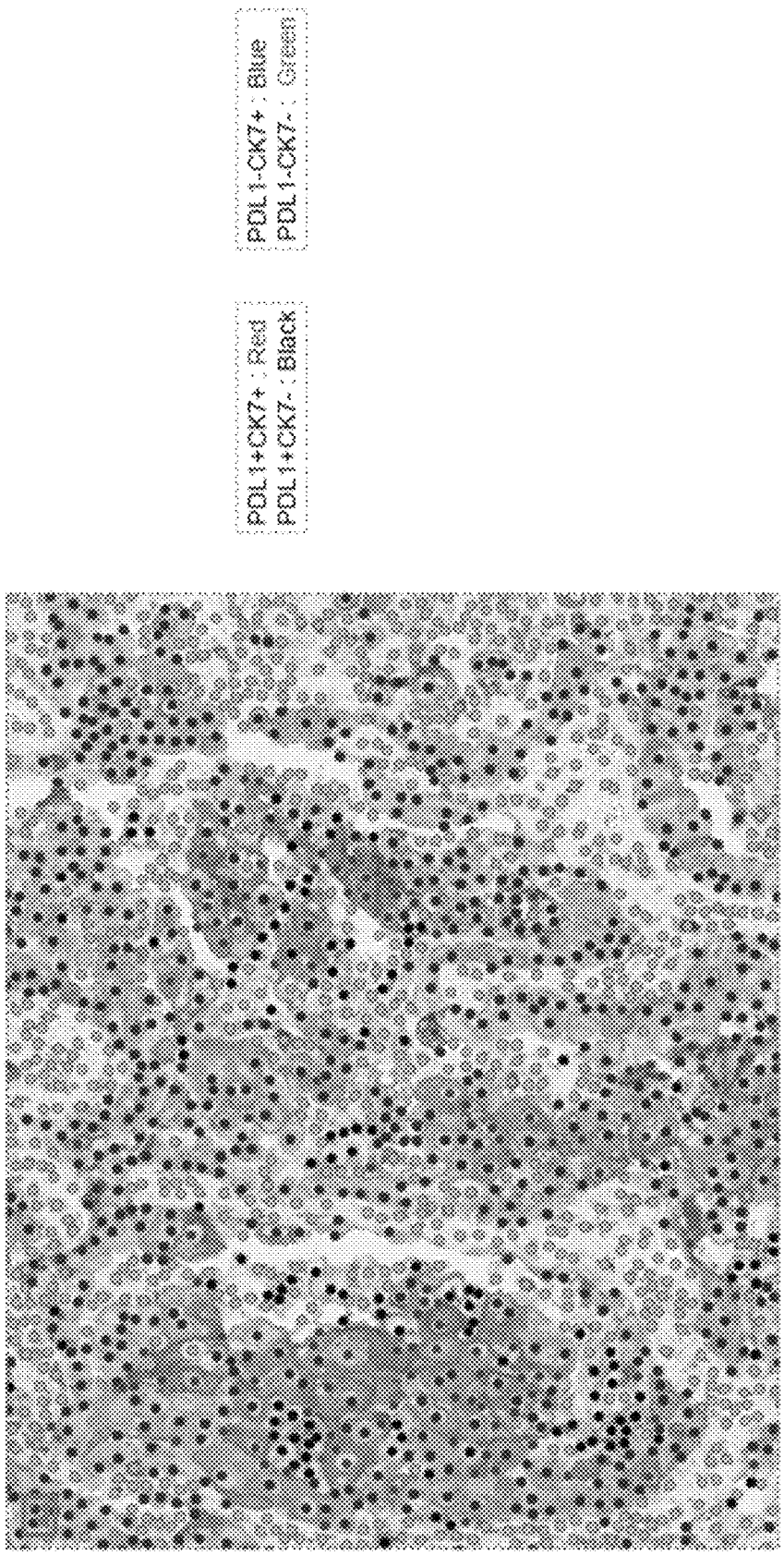
FIG. 11 shows an exemplary initial cell classification labels generated via a HALO analysis.
Figure 12:
FIG. 12 shows an exemplary tissue segmentation performed by the HALO analysis (segmenting into tumor, stroma, and background regions).
Figure 12:
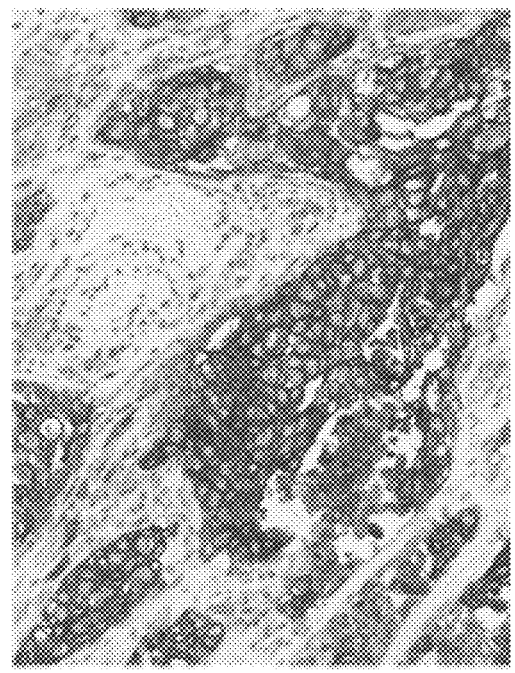

Each of multiple tissue slices were stained with novel chromogens—PDL1 was marked by Tamra (Tyramide-MATRA) and CK7 was marked by Dabsyl (QM—Dabsyl). FOVs were selected. For generation of groundtruth for PDL1/CK7, 40 FOVs were chosen by a pathologist from 4 different duplex slides. Following the selection of FOVs, HALO analysis was performed on all the duplex slides. The HALO analysis was a 2-step process. The first step was tissue segmentation and the second step was cell classification. FIG. 11 shows the initial cell classification labels generated via the HALO analysis. The HALO tissue segmentation classified the tissue into 3 classes—(i) Tumor (ii) Stroma (iii) Background. FIG. 12 shows the tissue segmentation performed by the HALO analysis (segmenting into tumor, stroma, and background regions), which indicates that segmentation performed by the HALO algorithm was quite poor.

Further, FIG. 13 overlays representations of the HALO cell classifications with a corresponding digital pathology slide. Multiple types of issues are apparent. For example, multiple benign epithelial cells showing Dabysl staining (marking CK7) had been assigned a classification by the HALO assessment. Further, multiple macrophages showed moderate to strong membrane staining that would represent detected PDL1+, though signals from macrophages may distort metrics generated by the digital-pathology analysis.

FIG. 14 further shows inconsistencies of the HALO outputs. For example, many cells in the stroma region that showed Tamra staining were detected as positively showing PDL1, despite the fact that it is inconsistent for a cell to be PDL1-positive and to be within a stroma region. As another example, the HALO outputs detected PDL1-positive cells within necrotic regions, while necrotic regions are indicative of cells dying.

FIGS. 15 and 16 show how scores representing relative quantities of PDL1-positive and CK7-positive cells (respectively) were determined based on the HALO results (yellow) compared to the relative quantities based on assessments from the consensus scores based on reviews from three pathologists.

Thus, the cell classifications performed using the HALO outputs were sub-optimal. Apart from inadequate tissue segmentation, HALO had other limitations as follows:

Benign epithelial cells showing Dabsyl staining were detected as CK7+

Macrophages showing moderate/strong membrane staining were detected as PDL1+

Lots of cells in stroma region showing Tamra staining had been detected as PDL1+

Multiple PDL1+ cells were incorrectly detected in the necrotic regions

Due to inadequate tissue segmentation and the above-mentioned limitations, HALO created many false positives.

Cell Classification using Interactive Segmentation and Deep-Learning Model

The same images were separately processed using a deep-learning model trained on multiple class data and an interactive GUI that supported labeling various segmented regions. At test time, the trained model was not modified any more, but took as model input the image of interest along with minimal user annotations, for example, mouse clicks, to segment the user clicked region of interest. As users provided more annotations, the model prediction adjusted accordingly. This approach often took less than one minute to segment an image tile of 600×600 pixels in size. With no model retraining or fine-tuning at test time, the model did not overfit to specific datasets and maintained its excellent generalizability. In addition, instead of being a black-box, such a platform enabled user-guided modifications of model prediction, which provided real-time feedback and thus was interactive, intuitive and flexible for end-users.

More specifically, the deep-learning model was trained on the Semantic Boundaries Dataset (SBD). SBD contained 11355 images, among which 8498 were used for training and 2857 for validation. An HRNet with OCR modules was pre-trained on ImageNet as its backbone.

The tissue segmentation performed using the deep-learning model was integrated with the HALO based cell classification results. On integration with the tissue segmentation, the number of classes for the cell phenotypes was 5, which were (i) PDL1+CK7+(ii) PDL1+CK7− (iii) PDL1−CK7+(iv) PDL1−CK7− and (v) Background.

As illustrated in FIG. 17, the tissue segmentation performed using the deep-learning model trained with multi-class data much more accurately characterized the tissue region into (i) Tumor (ii) Stroma and (iii) Background (i.e., Other) relative to the HALO segmentation.

HALO cell classifications were revised such that cells located within a Background region (using the segmentations generated by the deep-learning model) were reassigned to a new background cell-classification label. As indicated in FIG. 18, macrophages, anthracotic cells, necrotic regions etc. were then correctly classified as being within the 'Other' class.

The left and right graphs in FIG. 19 show scores representing a relative quantities of PDL1-positive and CK7-positive cells (respectively) as predicted based on the platform results generated based on modifying the deep-learning model's classifications based on region labels (yellow), compared to the relative quantities based on assessments from the consensus scores based on reviews from three pathologists. As in FIGS. 15-16, scores and errors generated based on reviews from three pathologists are also shown.

It can be seen that the proposed method is very much aligned with the pathologists' scores and thus could be validated as a very competitive method.

FIG. 20 provides a further example how processing of a digital pathology image (left image) differs depending on whether a traditional color unmixing technique is performed to attempt to isolate tumor signals (top right) or whether the above-identified approach (of modifying HALO cell classifications based on regions identified using a deep-learning model, bottom right).

In this instance, there were not many tumor negative examples (i.e. PDL1−CK7− tumor cells) in the training set. Therefore, synthetic hematoxylin-only (HTX-only) images were created from duplex images in order to generate synthetic tumor negative examples. The bottom right image shows examples of synthetic tumor negatives marked with green dots.

It can be seen that the image generated by modifying HALO signals based on outputs from a deep-learning model appears to have much sharper and more accurate signal outputs as compared to signals produced from the HALO cell-classification outputs. The annotations generated based on modifying HALO signals were compared to labels from a lead pathologist, and the error level was less than 5%.

Some embodiments of the present disclosure include a system including one or more data processors. In some embodiments, the system includes a non-transitory computer readable storage medium containing instructions which, when executed on the one or more data processors, cause the one or more data processors to perform part or all of one or more methods and/or part or all of one or more processes disclosed herein. Some embodiments of the present disclosure include a computer-program product tangibly embodied in a non-transitory machine-readable storage medium, including instructions configured to cause one or more data processors to perform part or all of one or more methods and/or part or all of one or more processes disclosed herein.

The terms and expressions which have been employed are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention as claimed has been specifically disclosed by embodiments and optional features, modification, and variation of the concepts herein disclosed may be resorted to by those skilled in the art, and that such modifications and variations are considered to be within the scope of this invention as defined by the appended claims.

The description provides preferred exemplary embodiments only, and is not intended to limit the scope, applicability or configuration of the disclosure. Rather, the description of the preferred exemplary embodiments will provide those skilled in the art with an enabling description for implementing various embodiments. It is understood that various changes may be made in the function and arrangement of elements without departing from the spirit and scope as set forth in the appended claims.

Specific details are given in the following description to provide a thorough understanding of the embodiments. However, it will be understood that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

What is claimed is:

1. A computer-implemented method comprising:
   accessing a digital pathology image that depicts a tissue slice stained with multiple stains, each of the multiple stains staining for a corresponding biomarker of a set of biomarkers, wherein the multiple stains include at least three stains;
   generating, using a first machine-learning model, a segmented image that identifies at least:
      a predicted diseased region in the digital pathology image; and
      a background region in the digital pathology image, wherein the background region indicates that signals that are present within the background region are not to be assessed when analyzing signals of the set of biomarkers;
   detecting depictions of a set of cells in the digital pathology image;
   generating, using a second machine-learning model, a cell classification for each cell of the set of cells, wherein the cell classification is selected from a set of potential classifications that indicate which, if any, of the set of biomarkers are expressed in the cell;
   detecting that a subset of the set of cells in the digital pathology image are within the background region; and
   in response to detecting that the subset of the set of cells in the digital pathology image are within the background region, updating the cell classification for each cell of at least some cells in the subset to be a background classification that was not included in the set of potential classifications.

2. The computer-implemented method of claim 1, further comprising:
   generating a training data set that includes the digital pathology and that includes an updated set of cell classifications that includes the updated cell classification for each cell in the subset;
   training a third machine-learning model using the training data set.

3. The computer-implemented method of claim 2, further comprising:
   detecting that each cell in another subset of cells in the digital pathology image has a cell classification that is inconsistent with a region in which the cell is depicted as being located; and
   setting a confidence metric for the cell classification of each cell in the other subset to be lower than a confidence level associated with different cell classifications that were not detected as being inconsistent with the region in which the cell is depicted as being located; wherein the third machine-learning model is trained using the confidence metrics.

4. The computer-implemented method of claim 2, further comprising:
   generating a new set of cell classifications by processing a different digital-pathology image using the third machine-learning model, wherein a new subset of the new set of cell classifications correspond to the background classification; and
   generating one or more metrics corresponding to a predicted diagnosis, prognosis or treatment response using the new set of cell classifications; and
   outputting the one or more metrics.

5. The computer-implemented method of claim 2, wherein the third machine-learning model includes a U-Net architecture.

6. The computer-implemented method of claim 1, wherein updating the cell classification for each cell of the at least some cells in the subset to the background classification includes automatically update the cell classification for each cell of all cells in the subset to the background classification.

7. The computer implemented method of claim 1, further comprising:
   configuring a graphical user interface (GUI) to present an interactive screen that:
      displays at least part of the segmented image;
      displays, for each of at least some of the set of cells, a representation of the cell that indicates both the cell classification and a location of the depiction of the cell in the digital pathology image; and
      provides a tool configured to receive input from a user that indicates an instruction to change one or more of the cell classifications of the at least some of the set of cells;
   detecting an interaction with the tool that represents an instruction to change the cell classification of a particular cell of the at least some of the set of cells; and
   updating, in response to the detected interaction, the changed cell classification for the particular cell, wherein the updated set of cell classifications includes the changed cell classification for the particular cell.

8. The computer-implemented method of claim 1, further comprising:
   detecting that each cell in another subset of cells in the digital pathology image has a cell classification that is inconsistent with a region in which the cell is depicted as being located; and
   automatically changing the cell classification of each cell in the other subset.

9. The computer-implemented method of claim 1, further comprising:
   generating one or more metrics corresponding to a predicted diagnosis, prognosis or treatment response using the set of cell classifications; and
   outputting the one or more metrics.

10. The computer-implemented method of claim 1, wherein the GUI is configured such that a region in the segmented image is depicted using a color that is representative of the type of region.

11. The computer-implemented method of claim 1, wherein, for each stain of the set of stains, a target of the stain is a nuclear target.

12. The computer-implemented method of claim 1, wherein, for each stain of the set of stains, a target of the stain is a cell-membrane target.

13. A system comprising:
one or more data processors; and
a non-transitory computer readable storage medium containing instructions which, when executed on the one or more data processors, cause the one or more data processors to perform a set of operations including:
- accessing a digital pathology image that depicts a tissue slice stained with multiple stains, each of the multiple stains staining for a corresponding biomarker of a set of biomarkers, wherein the multiple stains include at least three stains;
- generating, using a first machine-learning model, a segmented image that identifies at least:
  - a predicted diseased region in the digital pathology image; and
  - a background region in the digital pathology image, wherein the background region indicates that signals that are present within the background region are not to be assessed when analyzing signals of the set of biomarkers;
- detecting depictions of a set of cells in the digital pathology image;
- generating, using a second machine-learning model, a cell classification for each cell of the set of cells, wherein the cell classification is selected from a set of potential classifications that indicate which, if any, of the set of biomarkers are expressed in the cell;
- detecting that a subset of the set of cells in the digital pathology image are within the background region; and
- in response to detecting that the subset of the set of cells in the digital pathology image are within the background region, updating the cell classification for each cell of at least some cells in the subset to be a background classification that was not included in the set of potential classifications.

14. The system of claim 13, wherein the set of operations further comprises:
- generating a training data set that includes the digital pathology and that includes an updated set of cell classifications that includes the updated cell classification for each cell in the subset;
- training a third machine-learning model using the training data set.

15. The system of claim 13, wherein the set of operations further comprises:
- configuring a graphical user interface (GUI) to present an interactive screen that:
  - displays at least part of the segmented image;
  - displays, for each of at least some of the set of cells, a representation of the cell that indicates both the cell classification and a location of the depiction of the cell in the digital pathology image; and
  - provides a tool configured to receive input from a user that indicates an instruction to change one or more of the cell classifications of the at least some of the set of cells;
- detecting an interaction with the tool that represents an instruction to change the cell classification of a particular cell of the at least some of the set of cells; and
- updating, in response to the detected interaction, the changed cell classification for the particular cell,
wherein the updated set of cell classifications includes the changed cell classification for the particular cell.

16. The system of claim 13, wherein the set of operations further comprises:
- detecting that each cell in another subset of cells in the digital pathology image has a cell classification that is inconsistent with a region in which the cell is depicted as being located; and
- automatically changing the cell classification of each cell in the other subset.

17. The system of claim 13, wherein the set of operations further comprises:
- generating one or more metrics corresponding to a predicted diagnosis, prognosis or treatment response using the set of cell classifications; and
- outputting the one or more metrics.

18. The system of claim 13, wherein the GUI is configured such that a region in the segmented image is depicted using a color that is representative of the type of region.

19. A computer-program product tangibly embodied in a non-transitory machine-readable storage medium, including instructions configured to cause one or more data processors to perform a set of operations comprising:
- accessing a digital pathology image that depicts a tissue slice stained with multiple stains, each of the multiple stains staining for a corresponding biomarker of a set of biomarkers, wherein the multiple stains include at least three stains;
- generating, using a first machine-learning model, a segmented image that identifies at least:
  - a predicted diseased region in the digital pathology image; and
  - a background region in the digital pathology image, wherein the background region indicates that signals that are present within the background region are not to be assessed when analyzing signals of the set of biomarkers;
- detecting depictions of a set of cells in the digital pathology image;
- generating, using a second machine-learning model, a cell classification for each cell of the set of cells, wherein the cell classification is selected from a set of potential classifications that indicate which, if any, of the set of biomarkers are expressed in the cell;
- detecting that a subset of the set of cells in the digital pathology image are within the background region; and
- in response to detecting that the subset of the set of cells in the digital pathology image are within the background region, updating the cell classification for each cell of at least some cells in the subset to be a background classification that was not included in the set of potential classifications.

* * * * *